(12) United States Patent
Procter et al.

(10) Patent No.: US 12,283,389 B2
(45) Date of Patent: Apr. 22, 2025

(54) METHODS AND SYSTEMS FOR THE CONCURRENT GENERATION OF MULTIPLE SUBSTANTIALLY SIMILAR X-RAY BEAMS

(71) Applicant: Rapiscan Holdings, Inc., Hawthorne, CA (US)

(72) Inventors: Mark Procter, Wilmslow (GB); James Ollier, Huyton (GB); David Johnson, Stoke-onTrent (GB)

(73) Assignee: Rapiscan Holdings, Inc., Hawthorne, CA (US)

( * ) Notice: Subject to any disclaimer, the term of this patent is extended or adjusted under 35 U.S.C. 154(b) by 219 days.

(21) Appl. No.: 17/929,143

(22) Filed: Sep. 1, 2022

(65) Prior Publication Data
US 2023/0108499 A1 Apr. 6, 2023

Related U.S. Application Data

(60) Provisional application No. 63/261,991, filed on Oct. 1, 2021.

(51) Int. Cl.
  *G21K 1/04* (2006.01)
  *G01V 5/22* (2024.01)
(52) U.S. Cl.
  CPC .............. *G21K 1/046* (2013.01); *G01V 5/224* (2024.01); *G01V 5/228* (2024.01)
(58) Field of Classification Search
  CPC . A61B 6/06; A61B 6/405; G21K 1/04; G21K 1/046
  See application file for complete search history.

(56) References Cited

U.S. PATENT DOCUMENTS

| | | |
|---|---|---|
| 2,331,586 A | 10/1943 | Wasisco |
| 2,831,123 A | 4/1958 | Daly |
| (Continued) | | |

FOREIGN PATENT DOCUMENTS

| | | |
|---|---|---|
| CN | 1270318 A | 10/2000 |
| CN | 1493176 A | 4/2004 |
| (Continued) | | |

OTHER PUBLICATIONS

International Search Report for PCT/US22/75829, Jan. 10, 2023.
(Continued)

*Primary Examiner* — Chih-Cheng Kao
(74) *Attorney, Agent, or Firm* — Novel IP

(57) ABSTRACT

An adjustable collimator device for collimating a beam of energy emitted from a radiation source is disclosed. The collimator has an elongated plate-like body with a front-end and a rear-end. The collimator has a first set of emission apertures equally spaced around a central axis of the body that defines a zero-degree position. The first set of emission apertures are placed on the rear-end of the body and are configured to receive and sample a beam of energy entering the adjustable collimator device. A second set of apertures are placed proximate the front-end of the body. The second set of apertures are adjustable such that a first of the second set of apertures can be configured to have a first angular offset relative to the zero-axis and a second of the second set of apertures can be configured to have a second angular offset relative to the zero-axis.

19 Claims, 11 Drawing Sheets

(56) References Cited

U.S. PATENT DOCUMENTS

| | | |
|---|---|---|
| 2,972,430 A | 2/1961 | Johnson |
| 3,140,397 A | 7/1964 | Henry |
| 3,151,245 A | 9/1964 | Wilson, Jr. |
| 3,275,831 A | 9/1966 | Martin |
| 3,603,793 A | 9/1971 | Warren |
| 3,766,387 A | 10/1973 | Heffan |
| 3,780,291 A | 12/1973 | Stein |
| 3,784,837 A | 1/1974 | Holmstrom |
| 3,898,463 A | 8/1975 | Noakes |
| 3,961,186 A | 6/1976 | Leunbach |
| 3,971,948 A | 7/1976 | Pfeiler |
| 4,031,401 A | 6/1977 | Jacob |
| 4,031,545 A | 6/1977 | Stein |
| 4,045,672 A | 8/1977 | Watanabe |
| 4,047,035 A | 9/1977 | Dennhoven |
| 4,064,440 A | 12/1977 | Roder |
| 4,139,771 A | 2/1979 | Dennhoven |
| 4,143,273 A | 3/1979 | Richey |
| 4,160,165 A | 7/1979 | Mccombs |
| 4,180,737 A | 12/1979 | Kingsley |
| 4,200,800 A | 4/1980 | Swift |
| 4,203,036 A | 5/1980 | Tschunt |
| 4,210,811 A | 7/1980 | Dennhoven |
| 4,216,499 A | 8/1980 | Manfred |
| 4,228,357 A | 10/1980 | Annis |
| 4,242,583 A | 12/1980 | Annis |
| 4,242,588 A | 12/1980 | Huang |
| 4,259,582 A | 3/1981 | Albert |
| 4,260,898 A | 4/1981 | Annis |
| 4,267,446 A | 5/1981 | Brown |
| 4,315,146 A | 2/1982 | Rudin |
| 4,342,914 A | 8/1982 | Bjorkholm |
| 4,366,382 A | 12/1982 | Kotowski |
| 4,380,817 A | 4/1983 | Harding |
| 4,389,729 A | 6/1983 | Stein |
| 4,420,182 A | 12/1983 | Kaneshiro |
| 4,430,568 A | 2/1984 | Yoshida |
| 4,472,822 A | 9/1984 | Swift |
| 4,494,001 A | 1/1985 | Peck |
| 4,497,062 A | 1/1985 | Mistretta |
| 4,497,768 A | 2/1985 | Caldwell |
| 4,503,332 A | 3/1985 | Annis |
| 4,511,799 A | 4/1985 | Bjorkholm |
| 4,525,854 A | 6/1985 | Molbert |
| 4,566,113 A | 1/1986 | Gerhard |
| 4,599,740 A | 7/1986 | Cable |
| 4,620,099 A | 10/1986 | Schoenig |
| 4,641,330 A | 2/1987 | Herwig |
| 4,646,339 A | 2/1987 | Rice |
| 4,667,107 A | 5/1987 | Wang |
| 4,691,332 A | 9/1987 | Burstein |
| 4,692,937 A | 9/1987 | Sashin |
| 4,718,075 A | 1/1988 | Horn |
| 4,736,401 A | 4/1988 | Donges |
| 4,754,469 A | 6/1988 | Harding |
| 4,788,436 A | 11/1988 | Koechner |
| 4,788,704 A | 11/1988 | Donges |
| 4,789,930 A | 12/1988 | Sones |
| 4,799,247 A | 1/1989 | Annis |
| 4,807,637 A | 2/1989 | Bjorkholm |
| 4,809,312 A | 2/1989 | Annis |
| 4,825,454 A | 4/1989 | Annis |
| 4,839,913 A | 6/1989 | Annis |
| 4,864,142 A | 9/1989 | Gomberg |
| 4,870,670 A | 9/1989 | Geus |
| 4,884,289 A | 11/1989 | Glockmann |
| 4,897,550 A | 1/1990 | Bernard |
| 4,899,283 A | 2/1990 | Annis |
| 4,953,189 A | 8/1990 | Wang |
| 4,956,856 A | 9/1990 | Harding |
| 4,979,202 A | 12/1990 | Siczek |
| 4,991,189 A | 2/1991 | Boomgaarden |
| 5,006,299 A | 4/1991 | Gozani |
| 5,007,072 A | 4/1991 | Jenkins |
| 5,008,911 A | 4/1991 | Harding |
| 5,022,062 A | 6/1991 | Annis |
| 5,056,129 A | 10/1991 | Steinmeyer |
| 5,065,418 A | 11/1991 | Bermbach |
| 5,068,883 A | 11/1991 | DeHaan |
| 5,076,993 A | 12/1991 | Sawa |
| 5,077,771 A | 12/1991 | Skillicorn |
| 5,078,952 A | 1/1992 | Gozani |
| 5,091,924 A | 2/1992 | Bermbach |
| 5,098,640 A | 3/1992 | Gozani |
| 5,102,506 A | 4/1992 | Tanielian |
| 5,103,099 A | 4/1992 | Bourdinaud |
| 5,114,662 A | 5/1992 | Gozani |
| 5,127,030 A | 6/1992 | Annis |
| 5,153,439 A | 10/1992 | Gozani |
| 5,162,096 A | 11/1992 | Gozani |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis |
| 5,263,075 A | 11/1993 | McGann |
| 5,265,144 A | 11/1993 | Harding |
| 5,281,820 A | 1/1994 | Groh |
| 5,289,510 A | 2/1994 | Mihalczo |
| 5,302,817 A | 4/1994 | Yokota |
| 5,313,511 A | 5/1994 | Annis |
| 5,319,547 A | 6/1994 | Krug |
| 5,338,927 A | 8/1994 | De Groot |
| 5,343,046 A | 8/1994 | Smith |
| 5,367,552 A | 11/1994 | Peschmann |
| 5,376,795 A | 12/1994 | Hasegawa |
| 5,379,334 A | 1/1995 | Zimmer |
| 5,388,128 A | 2/1995 | Gozani |
| 5,391,878 A | 2/1995 | Petroff |
| 5,394,454 A | 2/1995 | Harding |
| 5,420,905 A | 5/1995 | Bertozzi |
| 5,420,959 A | 5/1995 | Walker |
| 5,430,787 A | 7/1995 | Norton |
| 5,446,288 A | 8/1995 | Tumer |
| 5,493,596 A | 2/1996 | Annis |
| 5,524,133 A | 6/1996 | Neale |
| 5,528,656 A | 6/1996 | Annis |
| 5,548,123 A | 8/1996 | Perez-Mendez |
| 5,550,380 A | 8/1996 | Sugawara |
| 5,600,144 A | 2/1997 | Worstell |
| 5,600,303 A | 2/1997 | Husseiny |
| 5,600,700 A | 2/1997 | Krug |
| 5,629,515 A | 5/1997 | Maekawa |
| 5,629,523 A | 5/1997 | Ngo |
| 5,638,420 A | 6/1997 | Armistead |
| 5,642,393 A | 6/1997 | Krug |
| 5,642,394 A | 6/1997 | Rothschild |
| 5,665,969 A | 9/1997 | Beusch |
| 5,666,393 A | 9/1997 | Annis |
| 5,687,210 A | 11/1997 | Maitrejean |
| 5,692,028 A | 11/1997 | Geus |
| 5,692,029 A | 11/1997 | Husseiny |
| 5,696,806 A | 12/1997 | Grodzins |
| 5,734,166 A | 3/1998 | Czirr |
| 5,745,543 A | 4/1998 | De Bokx |
| 5,751,837 A | 5/1998 | Watanabe |
| 5,763,886 A | 6/1998 | Schulte |
| 5,764,683 A | 6/1998 | Swift |
| 5,768,334 A | 6/1998 | Maitrejean |
| 5,783,829 A | 7/1998 | Sealock |
| 5,784,507 A | 7/1998 | Holm-Kennedy |
| 5,787,145 A | 7/1998 | Geus |
| 5,805,660 A | 9/1998 | Perion |
| 5,812,720 A | 9/1998 | Dannoux |
| 5,838,759 A | 11/1998 | Armistead |
| 5,856,673 A | 1/1999 | Ikegami |
| 5,866,907 A | 2/1999 | Drukier |
| 5,903,623 A | 5/1999 | Swift |
| 5,910,973 A | 6/1999 | Grodzins |
| 5,930,326 A | 7/1999 | Rothschild |
| 5,936,240 A | 8/1999 | Dudar |
| 5,940,468 A | 8/1999 | Huang |

(56) References Cited

U.S. PATENT DOCUMENTS

| | | |
|---|---|---|
| 5,968,425 A | 10/1999 | Bross |
| 5,974,111 A | 10/1999 | Krug |
| 6,018,562 A | 1/2000 | Willson |
| 6,031,890 A | 2/2000 | Bermbach |
| 6,054,712 A | 4/2000 | Komardin |
| 6,055,111 A | 4/2000 | Nomura |
| 6,058,158 A | 5/2000 | Eiler |
| 6,067,344 A | 5/2000 | Grodzins |
| 6,078,052 A | 6/2000 | Difilippo |
| 6,081,580 A | 6/2000 | Grodzins |
| 6,094,472 A | 7/2000 | Smith |
| 6,118,850 A | 9/2000 | Mayo |
| 6,128,365 A | 10/2000 | Bechwati |
| 6,151,381 A | 11/2000 | Grodzins |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,198,795 B1 | 3/2001 | Naumann |
| 6,203,846 B1 | 3/2001 | Ellingson |
| 6,212,251 B1 | 4/2001 | Tomura |
| 6,218,943 B1 | 4/2001 | Ellenbogexn |
| 6,236,709 B1 | 5/2001 | Perry |
| 6,249,567 B1 | 6/2001 | Rothschild |
| 6,252,929 B1 | 6/2001 | Swift |
| 6,256,369 B1 | 7/2001 | Lai |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,320,933 B1 | 11/2001 | Grodzins |
| 6,327,339 B1 | 12/2001 | Chung |
| 6,333,502 B1 | 12/2001 | Sumita |
| 6,356,620 B1 | 3/2002 | Rothschild |
| 6,407,392 B1 | 6/2002 | Tsuyuki |
| 6,421,420 B1 | 7/2002 | Grodzins |
| 6,424,695 B1 | 7/2002 | Grodzins |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,684 B1 | 9/2002 | Mun |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,542,754 B1 | 4/2003 | Sayers |
| 6,543,599 B2 | 4/2003 | Jasinetzky |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,567,496 B1 | 5/2003 | Sychev |
| 6,580,778 B2 | 6/2003 | Meder |
| 6,584,170 B2 | 6/2003 | Aust |
| 6,597,760 B2 | 7/2003 | Beneke |
| 6,606,516 B2 | 8/2003 | Levine |
| 6,621,888 B2 | 9/2003 | Grodzins |
| 6,628,745 B1 | 9/2003 | Annis |
| 6,636,581 B2 | 10/2003 | Sorenson |
| 6,637,266 B1 | 10/2003 | Froom |
| 6,645,656 B1 | 11/2003 | Chen |
| 6,645,657 B2 | 11/2003 | Huang |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |
| 6,687,326 B1 | 2/2004 | Bechwati |
| 6,702,459 B2 | 3/2004 | Barnes |
| 6,747,705 B2 | 6/2004 | Peters |
| 6,763,635 B1 | 7/2004 | Lowman |
| 6,785,357 B2 | 8/2004 | Bernardi |
| 6,798,863 B2 | 9/2004 | Sato |
| 6,812,426 B1 | 11/2004 | Kotowski |
| 6,816,571 B2 | 11/2004 | Bijjani |
| 6,837,422 B1 | 1/2005 | Meder |
| 6,839,403 B1 | 1/2005 | Kotowski |
| 6,843,599 B2 | 1/2005 | Le |
| 6,859,607 B2 | 2/2005 | Sugihara |
| 6,876,719 B2 | 4/2005 | Ozaki |
| 6,879,657 B2 | 4/2005 | Hoffman |
| 6,909,770 B2 | 6/2005 | Schramm |
| 6,911,251 B2 | 6/2005 | Duclos |
| 6,920,197 B2 | 7/2005 | Kang |
| 6,922,457 B2 | 7/2005 | Nagata |
| 6,922,460 B2 | 7/2005 | Skatter |
| 6,928,141 B2 | 8/2005 | Carver |
| 6,965,662 B2 | 11/2005 | Eppler |
| 7,010,094 B2 | 3/2006 | Grodzins |
| 7,039,159 B2 | 5/2006 | Muenchau |
| 7,067,079 B2 | 6/2006 | Bross |
| 7,072,440 B2 | 7/2006 | Mario |
| 7,092,485 B2 | 8/2006 | Kravis |
| 7,099,434 B2 | 8/2006 | Adams |
| 7,103,137 B2 | 9/2006 | Seppi |
| 7,106,830 B2 | 9/2006 | Rosner |
| 7,110,493 B1 | 9/2006 | Kotowski |
| 7,115,875 B1 | 10/2006 | Worstell |
| RE39,396 E | 11/2006 | Swift |
| 7,162,005 B2 | 1/2007 | Bjorkholm |
| 7,190,758 B2 | 3/2007 | Hagiwara |
| 7,203,276 B2 | 4/2007 | Arsenault |
| 7,207,713 B2 | 4/2007 | Lowman |
| 7,215,737 B2 | 5/2007 | Li |
| 7,217,929 B2 | 5/2007 | Hirai |
| 7,218,704 B1 | 5/2007 | Adams |
| 7,233,645 B2 | 6/2007 | Feda |
| 7,253,727 B2 | 8/2007 | Jenkins |
| 7,308,076 B2 | 12/2007 | Studer |
| 7,322,745 B2 | 1/2008 | Agrawal |
| 7,326,933 B2 | 2/2008 | Katagiri |
| 7,333,587 B2 | 2/2008 | De Man |
| 7,333,588 B2 | 2/2008 | Mistretta |
| 7,366,282 B2 | 4/2008 | Peschmann |
| 7,369,463 B1 | 5/2008 | Van Dullemen |
| 7,369,643 B2 | 5/2008 | Kotowski |
| 7,379,530 B2 | 5/2008 | Hoff |
| 7,400,701 B1 | 7/2008 | Cason |
| 7,403,588 B2 | 7/2008 | Bruder |
| 7,409,033 B1 | 8/2008 | Zhu |
| 7,409,042 B2 | 8/2008 | Bertozzi |
| 7,417,440 B2 | 8/2008 | Peschmann |
| 7,423,273 B2 | 9/2008 | Clayton |
| 7,486,768 B2 | 2/2009 | Allman |
| 7,496,178 B2 | 2/2009 | Turner |
| 7,505,556 B2 | 3/2009 | Chalmers |
| 7,505,562 B2 | 3/2009 | Dinca |
| 7,508,910 B2 | 3/2009 | Safai |
| 7,517,149 B2 | 4/2009 | Agrawal |
| 7,519,148 B2 | 4/2009 | Kotowski |
| 7,538,325 B2 | 5/2009 | Mishin |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,579,845 B2 | 8/2009 | Peschmann |
| 7,583,779 B2 | 9/2009 | Tkaczyk |
| 7,593,506 B2 | 9/2009 | Cason |
| 7,593,510 B2 | 9/2009 | Rothschild |
| 7,609,807 B2 | 10/2009 | Leue |
| 7,629,588 B1 | 12/2009 | Bell |
| 7,630,472 B2 | 12/2009 | Tsuyuki |
| 7,672,422 B2 | 3/2010 | Seppi |
| 7,711,090 B2 | 5/2010 | Schweizer |
| 7,720,195 B2 | 5/2010 | Allman |

(56) References Cited

U.S. PATENT DOCUMENTS

| | | |
|---|---|---|
| 7,742,557 B2 | 6/2010 | Brunner |
| 7,742,568 B2 | 6/2010 | Smith |
| 7,783,004 B2 | 8/2010 | Kotowski |
| 7,783,005 B2 | 8/2010 | Kaval |
| 7,796,733 B2 | 9/2010 | Hughes |
| 7,796,734 B2 | 9/2010 | Mastronardi |
| 7,809,109 B2 | 10/2010 | Mastronardi |
| 7,817,776 B2 | 10/2010 | Agrawal |
| 7,848,480 B2 | 12/2010 | Nakanishi |
| 7,856,079 B2 | 12/2010 | Nielsen |
| 7,856,081 B2 | 12/2010 | Peschmann |
| 7,864,920 B2 | 1/2011 | Rothschild |
| 7,876,880 B2 | 1/2011 | Kotowski |
| 7,924,979 B2 | 4/2011 | Rothschild |
| 7,963,695 B2 | 6/2011 | Kotowski |
| 7,995,705 B2 | 8/2011 | Allman |
| 7,995,707 B2 | 8/2011 | Rothschild |
| 7,999,236 B2 | 8/2011 | Mcdevitt |
| 8,000,436 B2 | 8/2011 | Seppi |
| 8,045,781 B2 | 10/2011 | Nakanishi |
| 8,054,938 B2 | 11/2011 | Kaval |
| 8,059,781 B2 | 11/2011 | Agrawal |
| 8,073,099 B2 | 12/2011 | Niu |
| 8,094,774 B2 | 1/2012 | Noshi |
| 8,135,110 B2 | 3/2012 | Morton |
| 8,135,112 B2 | 3/2012 | Hughes |
| 8,138,770 B2 | 3/2012 | Peschmann |
| 8,148,693 B2 | 4/2012 | Ryge |
| 8,194,822 B2 | 6/2012 | Rothschild |
| 8,199,996 B2 | 6/2012 | Hughes |
| 8,275,091 B2 | 9/2012 | Morton |
| 8,275,092 B1 | 9/2012 | Zhang |
| 8,275,093 B2 | 9/2012 | Rothschild |
| 8,300,763 B2 | 10/2012 | Shedlock |
| 8,325,871 B2 | 12/2012 | Grodzins |
| 8,331,535 B2 | 12/2012 | Morton |
| 8,345,819 B2 | 1/2013 | Mastronardi |
| 8,389,942 B2 | 3/2013 | Morton |
| 8,401,147 B2 | 3/2013 | Ryge |
| 8,428,217 B2 | 4/2013 | Peschmann |
| 8,433,036 B2 | 4/2013 | Morton |
| 8,439,565 B2 | 5/2013 | Mastronardi |
| 8,442,186 B2 | 5/2013 | Rothschild |
| 8,451,974 B2 | 5/2013 | Morton |
| 8,457,274 B2 | 6/2013 | Arodzero |
| 8,467,499 B2 | 6/2013 | Furth |
| 8,483,356 B2 | 7/2013 | Bendahan |
| 8,491,189 B2 | 7/2013 | Kotowski |
| 8,503,605 B2 | 8/2013 | Morton |
| 8,503,606 B2 | 8/2013 | Rothschild |
| 8,532,823 B2 | 9/2013 | Mcelroy |
| 8,576,982 B2 | 11/2013 | Gray |
| 8,582,720 B2 | 11/2013 | Morton |
| 8,605,859 B2 | 12/2013 | Mastronardi |
| 8,638,904 B2 | 1/2014 | Gray |
| 8,654,922 B2 | 2/2014 | Bendahan |
| 8,668,386 B2 | 3/2014 | Morton |
| 8,674,706 B2 | 3/2014 | Peschmann |
| 8,690,427 B2 | 4/2014 | Mastronardi |
| 8,731,137 B2 | 5/2014 | Arroyo, Jr. |
| 8,735,833 B2 | 5/2014 | Morton |
| 8,750,452 B2 | 6/2014 | Kaval |
| 8,750,454 B2 | 6/2014 | Gozani |
| 8,774,357 B2 | 7/2014 | Morton |
| 8,774,362 B2 | 7/2014 | Hughes |
| 8,798,232 B2 | 8/2014 | Bendahan |
| 8,804,899 B2 | 8/2014 | Morton |
| 8,824,632 B2 | 9/2014 | Mastronardi |
| 8,831,176 B2 | 9/2014 | Morton |
| 8,842,808 B2 | 9/2014 | Rothschild |
| 8,861,684 B2 | 10/2014 | Al-Kofahi |
| 8,884,236 B2 | 11/2014 | Rothschild |
| 8,885,794 B2 | 11/2014 | Morton |
| 8,903,045 B2 | 12/2014 | Schubert |
| 8,903,046 B2 | 12/2014 | Morton |
| 8,908,831 B2 | 12/2014 | Bendahan |
| 8,923,481 B2 | 12/2014 | Schubert |
| 8,929,509 B2 | 1/2015 | Morton |
| 8,958,526 B2 | 2/2015 | Morton |
| 8,971,487 B2 | 3/2015 | Mastronardi |
| 8,993,970 B2 | 3/2015 | Morton |
| 8,995,619 B2 | 3/2015 | Gray |
| 9,014,339 B2 | 4/2015 | Grodzins |
| 9,020,100 B2 | 4/2015 | Mastronardi |
| 9,020,103 B2 | 4/2015 | Grodzins |
| 9,025,731 B2 | 5/2015 | Kotowski |
| 9,036,779 B2 | 5/2015 | Morton |
| 9,042,511 B2 | 5/2015 | Peschmann |
| 9,052,271 B2 | 6/2015 | Grodzins |
| 9,052,403 B2 | 6/2015 | Morton |
| 9,057,679 B2 | 6/2015 | Morton |
| 9,069,084 B2 | 6/2015 | Frank |
| 9,069,101 B2 | 6/2015 | Arroyo, Jr. |
| 9,099,279 B2 | 8/2015 | Rommel |
| 9,117,564 B2 | 8/2015 | Rommel |
| 9,121,958 B2 | 9/2015 | Morton |
| 9,123,519 B2 | 9/2015 | Bendahan |
| 9,128,198 B2 | 9/2015 | Morton |
| 9,146,201 B2 | 9/2015 | Schubert |
| 9,158,030 B2 | 10/2015 | Morton |
| 9,182,516 B2 | 11/2015 | Gray |
| 9,183,647 B2 | 11/2015 | Morton |
| 9,194,828 B2 | 11/2015 | Turner |
| 9,207,195 B2 | 12/2015 | Gozani |
| 9,208,988 B2 | 12/2015 | Morton |
| 9,223,050 B2 | 12/2015 | Kaval |
| 9,251,915 B2 | 2/2016 | Lai |
| 9,257,208 B2 | 2/2016 | Rommel |
| 9,268,058 B2 | 2/2016 | Peschmann |
| 9,274,065 B2 | 3/2016 | Morton |
| 9,285,325 B2 | 3/2016 | Gray |
| 9,285,488 B2 | 3/2016 | Arodzero |
| 9,291,582 B2 | 3/2016 | Grodzins |
| 9,291,741 B2 | 3/2016 | Gray |
| 9,306,673 B1 | 4/2016 | Macrae |
| 9,316,760 B2 | 4/2016 | Bendahan |
| 9,417,060 B1 | 8/2016 | Schubert |
| 9,435,752 B2 | 9/2016 | Morton |
| 9,442,083 B2 | 9/2016 | Turner |
| 9,465,135 B2 | 10/2016 | Morton |
| 9,466,456 B2 | 10/2016 | Rommel |
| 9,535,019 B1 | 1/2017 | Rothschild |
| 9,541,510 B2 | 1/2017 | Arodzero |
| 9,562,866 B2 | 2/2017 | Morton |
| 9,576,766 B2 | 2/2017 | Morton |
| 9,606,245 B1 | 3/2017 | Czarnecki |
| 9,606,259 B2 | 3/2017 | Morton |
| 9,618,630 B2 | 4/2017 | Kross |
| 9,632,205 B2 | 4/2017 | Morton |
| 9,651,684 B1 | 5/2017 | Kusner |
| 9,658,343 B2 | 5/2017 | Arodzero |
| 9,791,590 B2 | 10/2017 | Morton |
| 9,823,201 B2 | 11/2017 | Morton |
| 9,835,756 B2 | 12/2017 | Morton |
| 9,841,386 B2 | 12/2017 | Grodzins |
| 9,915,752 B2 | 3/2018 | Peschmann |
| 9,958,569 B2 | 5/2018 | Morton |
| 10,134,254 B2 | 11/2018 | Jarvi |
| 10,168,445 B2 | 1/2019 | Morton |
| 10,209,372 B2 | 2/2019 | Arodzero |
| 10,228,487 B2 | 3/2019 | Mastronardi |
| 10,266,999 B2 | 4/2019 | Rothschild |
| 10,295,483 B2 | 5/2019 | Morton |
| 10,393,915 B2 | 8/2019 | Gozani |
| 10,408,967 B2 | 9/2019 | Morton |
| 10,535,491 B2 | 1/2020 | Rommel |
| 10,670,740 B2 | 6/2020 | Couture |
| 10,698,128 B2 | 6/2020 | Morton |
| 10,712,293 B2 | 7/2020 | Couture |
| 10,720,300 B2 | 7/2020 | Rommel |
| 10,724,192 B2 | 7/2020 | Rothschild |
| 10,746,674 B2 | 8/2020 | Morton |
| 10,754,057 B2 | 8/2020 | Bendahan |
| 10,762,998 B2 | 9/2020 | Rothschild |

(56) References Cited

U.S. PATENT DOCUMENTS

| | | |
|---|---|---|
| 10,770,195 B2 | 9/2020 | Rothschild |
| 10,794,843 B2 | 10/2020 | Rothschild |
| 10,830,911 B2 | 11/2020 | Couture |
| 10,901,113 B2 | 1/2021 | Morton |
| 10,955,367 B2 | 3/2021 | Couture |
| 10,976,465 B2 | 4/2021 | Morton |
| 11,119,245 B2 | 9/2021 | Morton |
| 11,143,783 B2 | 10/2021 | Morton |
| 11,300,703 B2 | 4/2022 | Morton |
| 11,340,361 B1 | 5/2022 | Couture |
| 11,371,948 B2 | 6/2022 | Morton |
| 11,397,276 B2 | 7/2022 | Bendahan |
| 11,448,606 B2 | 9/2022 | Rothschild |
| 11,525,930 B2 | 12/2022 | Couture |
| 11,561,320 B2 | 1/2023 | Morton |
| 11,726,218 B2 | 8/2023 | Couture |
| 11,822,041 B2 | 11/2023 | Morton |
| 2001/0016028 A1 | 8/2001 | Adams |
| 2001/0046275 A1 | 11/2001 | Hussein |
| 2002/0082492 A1 | 6/2002 | Grzeszczuk |
| 2002/0085674 A1 | 7/2002 | Price |
| 2002/0117625 A1 | 8/2002 | Pandelisev |
| 2002/0121604 A1 | 9/2002 | Katagiri |
| 2003/0002628 A1 | 1/2003 | Wilson |
| 2003/0108146 A1 | 6/2003 | Malamud |
| 2003/0223549 A1 | 12/2003 | Winsor |
| 2004/0004482 A1 | 1/2004 | Bouabdo |
| 2004/0057554 A1 | 3/2004 | Bjorkholm |
| 2004/0086078 A1 | 5/2004 | Adams |
| 2004/0104347 A1 | 6/2004 | Bross |
| 2004/0109653 A1 | 6/2004 | Kerr |
| 2004/0136493 A1 | 7/2004 | Konno |
| 2004/0140431 A1 | 7/2004 | Schmand |
| 2004/0141584 A1 | 7/2004 | Bernardi |
| 2004/0218714 A1 | 11/2004 | Faust |
| 2004/0251415 A1 | 12/2004 | Verbinski |
| 2004/0256565 A1 | 12/2004 | Adams |
| 2005/0018814 A1 | 1/2005 | Kerschner |
| 2005/0053199 A1 | 3/2005 | Miles |
| 2005/0058242 A1 | 3/2005 | Peschmann |
| 2005/0069081 A1 | 3/2005 | Kokubun |
| 2005/0073740 A1 | 4/2005 | Phillips |
| 2005/0078793 A1 | 4/2005 | Ikeda |
| 2005/0100124 A1 | 5/2005 | Hsieh |
| 2005/0105665 A1 | 5/2005 | Grodzins |
| 2005/0117700 A1 | 6/2005 | Peschmann |
| 2005/0135560 A1 | 6/2005 | Dafni |
| 2005/0180542 A1 | 8/2005 | Leue |
| 2005/0185757 A1 | 8/2005 | Kresse |
| 2005/0190878 A1 | 9/2005 | De Man |
| 2005/0226371 A1 | 10/2005 | Kautzer |
| 2005/0236577 A1 | 10/2005 | Katagiri |
| 2006/0067480 A1 | 3/2006 | Juschka |
| 2006/0078091 A1 | 4/2006 | Lasiuk |
| 2006/0188060 A1 | 8/2006 | Bertozzi |
| 2006/0251211 A1 | 11/2006 | Grodzins |
| 2007/0009088 A1 | 1/2007 | Edic |
| 2007/0019781 A1 | 1/2007 | Haras |
| 2007/0029493 A1 | 2/2007 | Kniss |
| 2007/0053495 A1 | 3/2007 | Morton |
| 2007/0064875 A1 | 3/2007 | Li |
| 2007/0098142 A1 | 5/2007 | Rothschild |
| 2007/0187608 A1 | 8/2007 | Beer |
| 2007/0206726 A1 | 9/2007 | Lu |
| 2007/0222981 A1 | 9/2007 | Ponsardin |
| 2007/0235655 A1 | 10/2007 | Rhiger |
| 2007/0237294 A1 | 10/2007 | Hoff |
| 2007/0258562 A1 | 11/2007 | Dinca |
| 2007/0280417 A1 | 12/2007 | Kang |
| 2008/0002806 A1 | 1/2008 | Nishide |
| 2008/0037707 A1 | 2/2008 | Rothschild |
| 2008/0043913 A1 | 2/2008 | Annis |
| 2008/0099692 A1 | 5/2008 | Poreira |
| 2008/0152081 A1 | 6/2008 | Cason |
| 2008/0175351 A1 | 7/2008 | Norman |
| 2008/0181357 A1 | 7/2008 | Bendahan |
| 2008/0191140 A1 | 8/2008 | Mcdevitt |
| 2008/0197279 A1 | 8/2008 | Kang |
| 2008/0198970 A1 | 8/2008 | Kirshner |
| 2008/0219804 A1 | 9/2008 | Chattey |
| 2008/0273652 A1 | 11/2008 | Arnold |
| 2009/0041197 A1 | 2/2009 | Clayton |
| 2009/0067575 A1 | 3/2009 | Seppi |
| 2009/0086907 A1 | 4/2009 | Smith |
| 2009/0103686 A1 | 4/2009 | Rothschild |
| 2009/0116617 A1 | 5/2009 | Mastronardi |
| 2009/0175412 A1 | 7/2009 | Grodzins |
| 2009/0188379 A1 | 7/2009 | Hiza |
| 2009/0213989 A1 | 8/2009 | Harding |
| 2009/0230295 A1 | 9/2009 | Waring |
| 2009/0230925 A1 | 9/2009 | Nathan |
| 2009/0257555 A1 | 10/2009 | Chalmers |
| 2009/0268871 A1 | 10/2009 | Rothschild |
| 2009/0274270 A1 | 11/2009 | Kotowski |
| 2009/0283690 A1 | 11/2009 | Bendahan |
| 2009/0309034 A1 | 12/2009 | Yoshida |
| 2010/0061509 A1 | 3/2010 | D Ambrosio |
| 2010/0069721 A1 | 3/2010 | Webler |
| 2010/0072398 A1 | 3/2010 | Fruehauf |
| 2010/0108859 A1 | 5/2010 | Andressen |
| 2010/0119033 A1 | 5/2010 | Li |
| 2010/0270462 A1 | 10/2010 | Nelson |
| 2010/0276602 A1 | 11/2010 | Clothier |
| 2010/0314546 A1 | 12/2010 | Ronda |
| 2010/0327174 A1 | 12/2010 | Edwards |
| 2011/0019799 A1 | 1/2011 | Shedlock |
| 2011/0064192 A1 | 3/2011 | Morton |
| 2011/0079726 A1 | 4/2011 | Kusner |
| 2011/0110490 A1 | 5/2011 | Samant |
| 2011/0116597 A1 | 5/2011 | Agrawal |
| 2011/0204243 A1 | 8/2011 | Bendahan |
| 2011/0206179 A1 | 8/2011 | Bendahan |
| 2011/0215222 A1 | 9/2011 | Eminoglu |
| 2011/0228896 A1 | 9/2011 | Peschmann |
| 2011/0309253 A1 | 12/2011 | Rothschild |
| 2011/0309257 A1 | 12/2011 | Menge |
| 2012/0033791 A1 | 2/2012 | Mastronardi |
| 2012/0043482 A1* | 2/2012 | Prince ............. G21K 1/046 250/505.1 |
| 2012/0061575 A1 | 3/2012 | Dunleavy |
| 2012/0076257 A1 | 3/2012 | Star-Lack |
| 2012/0104265 A1 | 5/2012 | Workman |
| 2012/0147987 A1 | 6/2012 | Calderbank |
| 2012/0148020 A1 | 6/2012 | Arroyo, Jr. |
| 2012/0155592 A1 | 6/2012 | Gozani |
| 2012/0199753 A1 | 8/2012 | Chuang |
| 2012/0241628 A1 | 9/2012 | Hesser |
| 2012/0280132 A1 | 11/2012 | Nakamura |
| 2012/0298864 A1 | 11/2012 | Morishita |
| 2013/0039463 A1 | 2/2013 | Mastronardi |
| 2013/0156156 A1 | 6/2013 | Roe |
| 2013/0188779 A1* | 7/2013 | Chao ............. A61N 5/01 378/150 |
| 2013/0195248 A1 | 8/2013 | Rothschild |
| 2013/0202089 A1 | 8/2013 | Schubert |
| 2013/0208857 A1 | 8/2013 | Arodzero |
| 2013/0315368 A1 | 11/2013 | Turner |
| 2013/0315369 A1 | 11/2013 | Turner |
| 2014/0105367 A1 | 4/2014 | Horvarth |
| 2014/0133631 A1 | 5/2014 | Wood |
| 2014/0182373 A1 | 7/2014 | Sbihli |
| 2014/0239204 A1 | 8/2014 | Orton |
| 2014/0270034 A1 | 9/2014 | Clayton |
| 2015/0016794 A1 | 1/2015 | Mori |
| 2015/0055751 A1 | 2/2015 | Funk |
| 2015/0060673 A1 | 3/2015 | Zimdars |
| 2015/0168589 A1 | 6/2015 | Morton |
| 2015/0185166 A1 | 7/2015 | Tang |
| 2015/0377803 A1 | 12/2015 | Turner |
| 2016/0025888 A1 | 1/2016 | Peschmann |
| 2016/0025889 A1 | 1/2016 | Morton |
| 2016/0033426 A1 | 2/2016 | Georgeson |
| 2016/0106384 A1 | 4/2016 | Park |
| 2016/0170044 A1 | 6/2016 | Arodzero |

(56) References Cited

U.S. PATENT DOCUMENTS

| | | | |
|---|---|---|---|
| 2016/0170077 A1 | 6/2016 | Morton |
| 2016/0223706 A1 | 8/2016 | Franco |
| 2017/0023695 A1 | 1/2017 | Zhang |
| 2017/0045630 A1 | 2/2017 | Simon |
| 2017/0059739 A1 | 3/2017 | Mastronardi |
| 2017/0184516 A1 | 6/2017 | Chen |
| 2017/0245819 A1 | 8/2017 | Rothschild |
| 2017/0299526 A1 | 10/2017 | Morton |
| 2017/0299764 A1 | 10/2017 | Morton |
| 2017/0315242 A1 | 11/2017 | Arodzero |
| 2017/0358380 A1 | 12/2017 | Rothschild |
| 2018/0038969 A1 | 2/2018 | Mccollough |
| 2018/0038988 A1 | 2/2018 | Morton |
| 2018/0128935 A1 | 5/2018 | Morton |
| 2018/0136340 A1 | 5/2018 | Nelson |
| 2018/0252841 A1 | 9/2018 | Grodzins |
| 2018/0284316 A1 | 10/2018 | Morton |
| 2018/0286624 A1 | 10/2018 | Rommel |
| 2018/0294066 A1 | 10/2018 | Rothschild |
| 2018/0313770 A1 | 11/2018 | Morton |
| 2018/0328861 A1 | 11/2018 | Grodzins |
| 2019/0139385 A1 | 5/2019 | Jarvi |
| 2019/0242834 A1 | 8/2019 | Rothschild |
| 2019/0293810 A1 | 9/2019 | Couture |
| 2019/0336795 A1* | 11/2019 | Zhou ............... A61N 5/1081 |
| 2019/0346382 A1 | 11/2019 | Rothschild |
| 2019/0383953 A1 | 12/2019 | Arodzero |
| 2019/0391280 A1 | 12/2019 | Couture |
| 2020/0025955 A1 | 1/2020 | Gozani |
| 2020/0033274 A1 | 1/2020 | Couture |
| 2020/0073008 A1 | 3/2020 | Parikh |
| 2020/0103357 A1 | 4/2020 | Morton |
| 2020/0103547 A1 | 4/2020 | Morton |
| 2020/0158908 A1 | 5/2020 | Morton |
| 2020/0191991 A1 | 6/2020 | Morton |
| 2020/0233100 A1 | 7/2020 | Rothschild |
| 2020/0326291 A1 | 10/2020 | Rothschild |
| 2020/0326436 A1 | 10/2020 | Couture |
| 2020/0355631 A1 | 11/2020 | Yu |
| 2020/0355632 A1 | 11/2020 | Morton |
| 2020/0381211 A1 | 12/2020 | Ren |
| 2021/0018650 A1 | 1/2021 | Morton |
| 2021/0132239 A1 | 5/2021 | Couture |
| 2021/0215846 A1 | 7/2021 | Morton |
| 2022/0003693 A1 | 1/2022 | Rothschild |
| 2022/0091054 A1 | 3/2022 | Rothschild |

FOREIGN PATENT DOCUMENTS

| | | |
|---|---|---|
| CN | 1745296 A | 3/2006 |
| CN | 1947001 | 4/2007 |
| CN | 101142497 A | 3/2008 |
| CN | 101166469 A | 4/2008 |
| CN | 101578534 A | 11/2009 |
| CN | 102519988 A | 6/2012 |
| CN | 104204854 A | 12/2014 |
| CN | 107193034 A | 9/2017 |
| CN | 107209282 A | 9/2017 |
| DE | 2639631 A1 | 3/1978 |
| DE | 4017100 A1 | 12/1990 |
| DE | 102013102749 A1 | 10/2013 |
| EP | 113291 A1 | 7/1984 |
| EP | 0261984 A2 | 3/1988 |
| EP | 0813692 A1 | 12/1997 |
| EP | 0864884 A2 | 9/1998 |
| EP | 0971215 A1 | 1/2000 |
| EP | 1113291 A1 | 7/2001 |
| EP | 1135700 | 9/2001 |
| EP | 1168249 A1 | 1/2002 |
| EP | 1254384 | 11/2002 |
| EP | 1733213 | 12/2006 |
| EP | 2049888 | 4/2009 |
| EP | 2054741 | 5/2009 |
| EP | 2663885 | 12/2014 |
| EP | 3271709 A1 | 1/2018 |
| FR | 2492159 | 4/1982 |
| GB | 1505498 A | 3/1978 |
| GB | 2084829 A | 4/1982 |
| GB | 2150526 A | 7/1985 |
| GB | 2277013 A | 10/1994 |
| GB | 2299251 | 9/1996 |
| GB | 2400480 A | 10/2004 |
| GB | 2463550 | 3/2010 |
| GB | 2482024 A | 1/2012 |
| JP | 58103678 | 6/1983 |
| JP | 62147349 A | 7/1987 |
| JP | S63299100 | 12/1988 |
| JP | 10232284 A | 2/1997 |
| JP | H09318757 A | 12/1997 |
| JP | H10185842 | 7/1998 |
| JP | H10232284 A | 9/1998 |
| JP | 2000515629 | 11/2000 |
| JP | 2002071816 A | 3/2002 |
| JP | 2004045250 A | 2/2004 |
| JP | 2006505805 | 2/2006 |
| JP | 2007532876 | 11/2007 |
| JP | 2013205122 | 10/2013 |
| JP | 3195776 | 2/2015 |
| KR | 102006132990 | 12/2006 |
| WO | 9701089 | 1/1997 |
| WO | 1997001089 A1 | 1/1997 |
| WO | 9802763 A | 1/1998 |
| WO | 1998003889 A1 | 1/1998 |
| WO | 9805946 A1 | 2/1998 |
| WO | 1998020366 A1 | 5/1998 |
| WO | 9913323 A2 | 3/1999 |
| WO | 9939189 | 8/1999 |
| WO | 2000033060 | 6/2000 |
| WO | 2000037928 A2 | 6/2000 |
| WO | 0159485 A1 | 8/2001 |
| WO | 0173415 A2 | 10/2001 |
| WO | 02091023 A2 | 11/2002 |
| WO | 03075037 A1 | 9/2003 |
| WO | 2004010127 A1 | 1/2004 |
| WO | 2004043740 A2 | 5/2004 |
| WO | 2004097889 A2 | 11/2004 |
| WO | 2005079437 A2 | 9/2005 |
| WO | 2005098400 | 10/2005 |
| WO | 2005103759 A1 | 11/2005 |
| WO | 2006111323 A2 | 10/2006 |
| WO | 2006137932 A2 | 12/2006 |
| WO | 2007051092 A2 | 5/2007 |
| WO | 2008021807 A2 | 2/2008 |
| WO | 2008024825 A2 | 2/2008 |
| WO | 2008063695 A2 | 5/2008 |
| WO | 2008105782 A2 | 9/2008 |
| WO | 2009027667 A2 | 3/2009 |
| WO | 2009067394 A2 | 5/2009 |
| WO | 2009129816 A1 | 10/2009 |
| WO | 2009137985 A1 | 11/2009 |
| WO | 2010129926 A1 | 11/2010 |
| WO | 2011008718 A1 | 1/2011 |
| WO | 2011011583 A1 | 1/2011 |
| WO | 2011014445 A1 | 2/2011 |
| WO | 2011053972 A2 | 5/2011 |
| WO | 2011149566 A2 | 12/2011 |
| WO | 2011163108 A2 | 12/2011 |
| WO | 2012058207 A2 | 5/2012 |
| WO | 2012109307 A1 | 8/2012 |
| WO | 2012142453 A2 | 10/2012 |
| WO | 2012142456 A2 | 10/2012 |
| WO | 2012174265 A1 | 12/2012 |
| WO | 2013112819 A1 | 8/2013 |
| WO | 2013116058 A1 | 8/2013 |
| WO | 2013116549 A1 | 8/2013 |
| WO | 2013122763 A1 | 8/2013 |
| WO | 2014058495 A2 | 4/2014 |
| WO | 2015020710 A2 | 2/2015 |
| WO | 2016003547 A1 | 1/2016 |
| WO | 2016081881 A1 | 5/2016 |
| WO | 2018064434 | 4/2018 |

(56) References Cited

FOREIGN PATENT DOCUMENTS

| | | | |
|---|---|---|---|
| WO | 2019217596 | A1 | 11/2019 |
| WO | 2020041161 | A1 | 2/2020 |

OTHER PUBLICATIONS

Written Opinion of the International Searching Authority for PCT/US22/75829, Jan. 10, 2023.
"Linac based photofission inspection system employing novel detection concepts", Nuclear Instruments and Methods (2011), vol. 653, Stevenson et al., pp. 124-128.
"Multileaf collimators: modern beam shaping," http://medphys365.blogspot.com/2012/04/multileaf-collimators.html (Year: 2012).
Accatino M R et al, "The nuclear car wash: a scanner to detect illicit special nuclear material in cargo containers", IEEE Sensors Journal, IEEE Service Center, NY, US, vol. 5, No. 4, Aug. 1, 2005, pp. 560-564, XP011136145.
*American Science & Engineering, Inc. v. Viken Detection Corp.*, U.S.D.C. (D. Mass.) Case No. 1:20-cv-11883-LTS, Joint Proposed Scheduling Order (Doc. 63), filed Oct. 12, 2021.
American Science and Engineering, Inc. 2002 Annual Report.
Appendix C—U.S. Pat. No. 7,505,562 Invalidity Claim Chart.
Appendix D—U.S. Pat. No. 8,300,763 Claim Charts.
AS& E's Opposition to Viken's Motion for Rule 11 Sanctions, Dkt. 38, Case 1:20-cv-11883 (Dist. of Mass.), Feb. 26, 2021.
AS&E pulls in $4.4M deal from U.S. agency, Apr. 27, 2009, downloaded from the following URL https://www.bizjournals.com/boston/blog/mass-high-tech/2009/04/ase-pulls-in-44m-deal-from-us-agency.html.
*AS&E v. Viken*, Defendant Viken Detection Corp.'s Preliminary Patent Related DisclosuresCase No. 1:20-cv-11833-LTS, United States District Court for the District of Massachusetts, Jan. 7, 2022.
Barnabe-Heider et al.: 'Characterization of the Response of Superheated Droplet (Bubble) Detectors.' Arxiv.org, [Online] Nov. 14, 2003, pp. 1-2 Retrieved from the Internet: <URL:http://arxiv.org/PS_cache/hep-ex/pdf/0311/0311034v1.pdf> [retrieved on Nov. 8, 2011].
Beznosko et al., "FNAL-NICADD Extruded Scintillator," FERMILAB-CONF-04-216-E, pp. 1-4 (Sep. 2004).
Case et al., "Wavelength-shifting fiber readout of LaC13 and LaBr3 scintillators," Proc. of SPIE, vol. 5898, UV, X-Ray, and Gamma-Ray Space Instrumentation for Astronomy XIV, pp. 58980K-1-58980K-8 (2005).
Chambers Dictionary of Science and Tech. (1999) (definition of "weighting observation").
Chapter 10, Ghilani, Adjustment Computations: Spatial Data Analysis, Sixth Edition, 2017 John Wiley & Sons, Inc. ("Weights of Observations").
Cheng et al, "Dynamic radiography using a carbonnanotube-based field emission x-ray source," Review of Scientific Instruments, vol. 75, No. 10. Oct. 2004.
Chou, C, "Fourier coded-aperture imaging in nuclear medicine", IEEE Proc. Sci. Meas. Technol., vol. 141. No. 3, May 1994, pp. 179-184.
Declaration of Richard C. Lanza, Ph.D., Case No. IPR2022-00027, U.S. Pat. No. 8,300,763, Oct. 20, 2021.
Declaration of Richard C. Lanza, Ph.D.,, Case No. IPR2021-01585; U.S. Pat. No. 7,400,701, Sep. 29, 2021.
Declaration of Richard Lanza, Ph.D., Case No. IPR2022-00028; U.S. Pat. No. 7,505,562, Oct. 28, 2021.
Defense Dept. contracts for X-ray tech, Apr. 7, 2009 downloaded from the following URL https://www.upi.com/Defense-News/2009/04/07/Defense-Dept-contracts-for-X-ray-tech/61051239114877/.
International Search Report and Written Opinion of the International Searching Authority, PCT/US2005/011382, Oct. 21, 2005.
European Patent Office, International Search Report, International Application No. PCT/US99/28266, dated Sep. 6, 2000, 3 pages.
Evans, R. D., The Atomic Nucleus, Ch. 23-25, & Appendix A, Tata McGraw-Hill, Bombay, New Delhi (1955).
Gundiah, "Scintillation properties of Eu.sup.2+-activated barium fluoroiodide," Lawrence Berkeley National Laboratory, pp. 1-10 (Feb. 2011).
https://en.wikipedia.org/wiki/ISM_band#Common_non-ISM_uses., downloaded from Internet Nov. 23, 2020.
Hutchinson et al., "Optical Readout for Imaging Neutron Scintillation Detectors," Engineering Science and Technology Division, Oak Ridge National Laboratory, Oak Ridge, Tennessee, 6 pages. (Nov. 2002).
International Preliminary Report on Patentability, PCT/US2005/011382, dated Oct. 19, 2006, 7 pages.
International Seach Report for PCT/US2008/083741, Oct. 30, 2009.
International Search Report and Written Opinion for PCT/US2010/041757, Oct. 12, 2010.
International Search Report for PCT/US01/09784, Jan. 28, 2002.
International Search Report for PCT/US02/13595, Aug. 6, 2002.
International Search Report for PCT/US03/05958, Jun. 27, 2003.
International Search Report for PCT/US03/35232, Nov. 8, 2004.
International Search Report for PCT/US11/23143, Nov. 25, 2011.
International Search Report for PCT/US11/26369, Nov. 22, 2011.
International Search Report for PCT/US14/37571, Mar. 16, 2015.
International Search Report for PCT/US17/54211, Jan. 18, 2018.
International Search Report for PCT/US20/61866, Feb. 11, 2021.
International Search Report for PCT/US2005/011382, Oct. 21, 2005.
International Search Report for PCT/US2006/060158, Jul. 5, 2007.
International Search Report for PCT/US2007/075323, Feb. 5, 2008.
International Search Report for PCT/US2007/076497, Jul. 28, 2008.
International Search Report for PCT/US2010/043201, Oct. 29, 2010.
International Search Report for PCT/US2011/041033, Feb. 17, 2012.
International Search Report for PCT/US2012/024248, Jul. 9, 2012.
International Search Report for PCT/US2012/033581, Oct. 31, 2012.
International Search Report for PCT/US2012/033585, Nov. 29, 2012.
International Search Report for PCT/US2013/022715, May 15, 2013.
International Search Report for PCT/US2013/023125, May 15, 2013.
International Search Report for PCT/US2013/024585, Jun. 2, 2013.
International Search Report for PCT/US2015/031115, Jul. 29, 2015.
International Search Report for PCT/US2016/023240, Jul. 12, 2016.
International Search Report for PCT/US2019/027242, Jul. 17, 2019.
International Search Report for PCT/US2019/027252, Aug. 2, 2019.
International Search Report for PCT/US99/29185, Sep. 27, 2000.
International Search Report, PCT/US1998/18642, dated Jul. 7, 1999, 4 pages.
International Search Report, PCT/US1999/028035, dated Sep. 15, 2000, 6 pages.
International Search Report, PCT/US2007/066936; dated: Sep. 30, 2008, 5 pages.
Jae Yul Ahn, Authorized officer Korean Intellectual Property Office, International Search Report—Application No. PCT/US2013/024585, date of mailing Jun. 2, 2013, along with Written Opinion of the International Searchi . . . .
Johns, H., & Cunningham J. R., "The Production and Properties of X Rays," Chapter 2, The Physics of Radiology, Charles C. Thomas Publisher, Springfield, IL, 4th Ed. (1983).
Jupiter, CP. and Parez, J. "A Study of the Scintillation Properties of Various Hydrogenous and Non-Hydrogenous Solutes Dissolved in Hexafluorobenzene" IEEE Transactions on Nuclear Science, Feb. 1966, pp. 692-703.
Keizer, "The optimal cosmic ray detector for High-Schools," 21 pages (2011).
Knoll, G. F., Radiation Detection and Measurements, Ch. 2, 4, 8, & 9, Third Edition, John Wiley & Sons, Inc. New York (2000).
Little, R.C.; Chadwick, M. B.; and Myers, W.L. "Detection of Highly Enriched Uranium Through Active Interrogation" Proceedings of the 11th International Conference on Nuclear Reaction Mechanics in Varenna, Italy, Jun. 2006.

(56) References Cited

OTHER PUBLICATIONS

Maekawa et al., "Thin Beta-ray Detectors using Plastic Scintillator Combined with Wavelength-shifting Fibers for Surface Contamination Monitoring," J. Nucl. Sci. Technol., vol. 35, No. 12, pp. 886-894 (Dec. 1998).
Mertz, L.N., et al, "Rotational aperture synthesis for x rays", Journal. Optical Society of America, vol. 3, Dec. 1986, pp. 2167-2170.
Moiseev et al., "High-efficiency plastic scintillator detector with wavelength-shifting fiber readout for the GLAST Large Area Telescope," Nucl. Instrum. Meth. Phys. Res. A, vol. 583, pp. 372-381 (2007).
Motion Hearing Transcript, dated Aug. 16, 2021, Case 1:20-cv-11883 (Dist. of Mass.).
Nishikido et al. "X-ray detector made of plastic scintillators and WLS fiber for real-time dose distribution monitoring in interventional radiology," IEEE Nuclear Science Symposium and Medical Imaging Conference Reco, pp. 1272-1274 (2012).
Nittoh et al., "Discriminated neutron and X-ray radiography using multi-color scintillation detector," Nuclear Instruments and Methods in Physics Research A, vol. 428, pp. 583-588 (1999).
Novikov, "A method for monitoring of Gd concentration in Gd-loaded scintillators," Nuclear Instruments and Methods in Physics Research A, vol. 366, pp. 413-414 (1995).
Osswald et al. "Injection Molding Handbook", p. 394, Chemical Industry Press, Mar. 31, 2005.
Pla-Dalmau et al., "Extruded Plastic Scintillator for Minerva," FERMILAB-CONF-05-506-E, pp. 1298-1300 (2005).
Roderick D. Swift, Roy P. Lindquist, "Medium energy x-ray examination of commercial trucks", Proc. SPIE 2276, Cargo Inspection Technologies, (Oct. 6, 1994); doi: 10.1117/12.189174.
Rose, Kathryn, "NuMI Off-Axis Experiment" Datasheet (online). University of Oxford & Rutherford Appleton Laboratory, 2003. <URL: https://slideplayer.com/slide/8765673/>.
Tateno, Y., & Tanaka, H., "Low-Dosage X-Ray Imaging System Employing Flying Spot X-Ray Microbeam (Dynamic Scanner)1," Radiation Physics, 121(1):189-195 (1976).
Tsahi Gozani et al, "Neuron threshold activation detectors (TAD) for the detection of fissions", Nuclear Instruments & methods in physics research, section A: Accelerators, Spectrometers, Detectors, and Associated Equipment, vol. 652, No. 1, Jan. 15, 2011, pp. 334-337, XP028291647, ISSN: 0168-9002.
U.S. Pat. No. 7,505,562 Prosecution File History.
U.S. Pat. No. 7,400,701 Prosecution File History.
U.S. Pat. No. 8,300,763 Prosecution File History.
U.S. Appl. No. 61/423,582 ("Gray '582"), filed Dec. 15, 2010.
U.S. Appl. No. 60/737,471, filed Nov. 17, 2005.
U.S. Appl. No. 60/787,810, filed Mar. 31, 2006.
U.S. Appl. No. 61/228,335 (priority document for '763 Patent), filed Jul. 24, 2009.
*Viken Detection Corporation v. AS&E*, Case No. IPR2021-01585, Petition for Inter Partes Review of U.S. Pat. No. 7,400,701, Sep. 30, 2021.
*Viken Detection Corporation v. AS&E*, Case No. IPR2022-00028, Petition for Inter Partes Review of U.S. Pat. No. 7,505,562, Oct. 28, 2021.
*Viken Detection Corporation v. AS&E*, Petition for Inter Partes Review, Case No. IPR2022-00027, U.S. Pat. No. 8,300,763, Oct. 20, 2021.
Viken's Memorandum of Law in Support of Defendant's Motion for Rule 11 Sanctions, Dkt. 30, Case 1:20-cv-11883 (Dist. of Mass.), Feb. 8, 2021.
Wait, G.D. "A Hexafluorobenzene Gamma Disimeter for Use in Mixed Neutron and Gamma Fields" Jan. 1968, AD0678658, Abstract.
Waiver of the Service of Summons, Oct. 20, 2020; Dkt. 6, Case 1:20-cv-11883, (Dist. of Mass.).
Williams et al.:"PET Detector Using Waveshifting Optical Fibers and Microchannel Plate PMT with Delay Line Readout", IEEE Transactions on Nuclear Science, IEEE Service Center, New York, NY, US, vol. 45, No. 2, Apr. 1, 1998 (Apr. 1, 1998), pp. 195-205, XP011087844, ISSN: 0018-9499, DOI: 10.1109/23.664171.
Wolf, A., Moreh, R., "Utilization of teflon-covered GE(Li) diodes for fast neutron detection," Nuclear Instruments and Methods, 148, 1978, 195-197.
Written Opinion of the International Searching Authority, PCT/US2007/066936, dated Sep. 30, 2008, 7 pages.
Yoshiaki et al. "Development of ultra-high sensitivity bioluminescent enzyme immunoassay for prostate-specific antigen (PSA) using firefly luciferas", Abstract, Luminescence, vol. 16, Issue 4, Jul. 31, 2001.
Yoshimura et al., "Plastic scintillator produced by the injection-molding technique," Nucl. Instr. Meth. Phys. Res. A, vol. 406, pp. 435-441 (1998).
Z Portal for Trucks & Cargo, Multi-View, Multi-Technology, Cargo and Vehicle Screening System, 2022 downloaded from the following URL: https://www.rapiscan-ase.com/products/portal/z-portal-for-trucks-cargoscreening.
Zhang et al, "A multi-beam x-ray imaging system based on carbon nanotube field emitters", Proceedings of SPIE vol. 6142, 614204, (2006), doi: 10.1117/12.654006.
Zhang et al., "A nanotube-based field emission x-ray source for microcomputed tomography", Review of Scientific Instruments 76, 094301 (2005).
Zhang et al., "Stationary scanning x-ray source based on carbon nanotube field emitters", Applied Physics Letters 86, 184104 (2005).
Notice of Allowance for U.S. Appl. No. 11/737,317, Sep. 9, 2008.
Applicant Response to Non-Final Office Action for U.S. Appl. No. 11/737,317, Apr. 30, 2008.
Non-Final Office Action for U.S. Appl. No. 11/097,092, May 15, 2006.
Non-Final Office Action for U.S. Appl. No. 11/737,317, Mar. 25, 2008.
Notice of Allowance for U.S. Appl. No. 11/097,092, Mar. 24, 2008.
Certificate of Correction for U.S. Pat. No. 7,400,701, Jul. 15, 2008.
Applicant Response to Non-Final Office Action for U.S. Appl. No. 11/097,092, Nov. 2, 2007.
Non-Final Office Action for U.S. Appl. No. 11/097,092, Aug. 20, 2007.
Applicant Response to Final Office Action and Advisory Action for U.S. Appl. No. 11/097,092, Jul. 3, 2007.
Applicant Response to Final Office Action for U.S. Appl. No. 11/097,092, Jun. 18, 2007.
Advisory Action Before the Filing of an Appeal Brief for U.S. Appl. No. 11/097,092, Jun. 21, 2007.
Final Office Action for U.S. Appl. No. 11/097,092, Mar. 21, 2007.
Non-Final Office Action for U.S. Appl. No. 11/097,092, Nov. 22, 2006.
Applicant Response to Non-Final Office Action for U.S. Appl. No. 11/097,092, Mar. 13, 2007.
Applicant Response to Non-Final Office Action for U.S. Appl. No. 11/097,092, Aug. 31, 2006.
Notice of Allowance for U.S. Appl. No. 11/737,317, Nov. 20, 2008.
Information Disclosure Statement for U.S. Appl. No. 11/737,317, Nov. 6, 2008.
Plaintiff AS&E's Infringement Contentions Chart, U.S. Pat. No. 11,143,783, *American Science & Engineering, Inc. v. Viken Detection Corp.*, C.A. 1:20-cv-11883, D. Mass.
https://www.vikendetection.com/news/viken-introduces-under-vehicle-scanner-cbp-plans-evaluation, Nov. 12, 2019, downloaded from Internet on Jan. 9, 2023.
Second Amended Complaint, *American Science & Engineering, Inc. v. Viken Detection Corp.*, C.A. 1:20-cv-11883, Dkt. 91, D. Mass. (Apr. 1, 2022).
U.S. Appl. No. 61/224,938, filed Jul. 13, 2009.
Declaration of Richard C. Lanza, Ph.D.,, Case No. PGR2022-00047, U.S. Pat. No. 11,143,783, Jul. 11, 2022.
Complaint, *American Science & Engineering, Inc. v. Viken Detection Corp.*, C.A. 1:20-cv-11883, Dkt. 1, D. Mass. (Oct. 19, 2020).
Denying Institution of Post-Grant Review for U.S. Pat. No. 11,143,783, Dec. 16, 2022.
Post-Grant Review Petition of U.S. Pat. No. 11,143,783, Jul. 11, 2022.

(56) References Cited

OTHER PUBLICATIONS https://www.krgv.com/videos/cbp-to-enhance-scanning-technology-at-southern-border-land-ports/, downloaded from Internet on Jan. 9, 2023.
https://www.foxnews.com/tech/border-technology-combat-illegal-smuggling, Jun. 16, 2020, downloaded from Internet on Jan. 9, 2023.
https://www.businesswire.com/news/home/20200323005617/en/Viken-Detection-Issues-Statement-on-ASE-Lawsuit, Mar. 23, 2020, downloaded from Internet on Jan. 9, 2023.
File History of U.S. Pat. No. 11,143,783—Part 1 of 6.
File History of U.S. Pat. No. 11,143,783—Part 2 of 6.
File History of U.S. Pat. No. 11,143,783—Part 3 of 6.
File History of U.S. Pat. No. 11,143,783—Part 4 of 6.
File History of U.S. Pat. No. 11,143,783—Part 5 of 6.
File History of U.S. Pat. No. 11,143,783—Part 6 of 6.
Non-Final Office Action for U.S. Appl. No. 17/195,505, May 17, 2021.
Applicant Response to Non-Final Office Action for U.S. Appl. No. 17/195,505, Jun. 7, 2021.
Notice of Allowance for U.S. Appl. No. 17/195,505, Jun. 29, 2021.
Notice of Allowance for U.S. Appl. No. 17/195,505, Jul. 9, 2021.
International Search Report for PCT/US13/24191, Rapiscan Systems Inc., mailed on Jun. 25, 2013.
Hutchinson D P et al: "Wavelength-shifting fiber readout of scintillation detectors", Jun. 30, 2001 (Jun. 30, 2001), pp. 1-14, XP93025861, Berlin; Retrieved from the Internet: URL:https://technicalreports.ornl.gov/cppr/y2001/pres/111170.pdf [retreived on Feb. 21, 2023].
McKnight et al: "The flexible embedded-fiber neutron detector", Nuclear Instruments & Methods in Physics Research. Section A, Elsevier BV * North-Holland, NL, vol. 586, No. 2, Dec. 3, 2007 (Dec. 3, 2007), pp. 246-250, XP022457692, ISSN: 0168-9002, DOI: 10.1016/J.NIMA.2007.11.044.

* cited by examiner

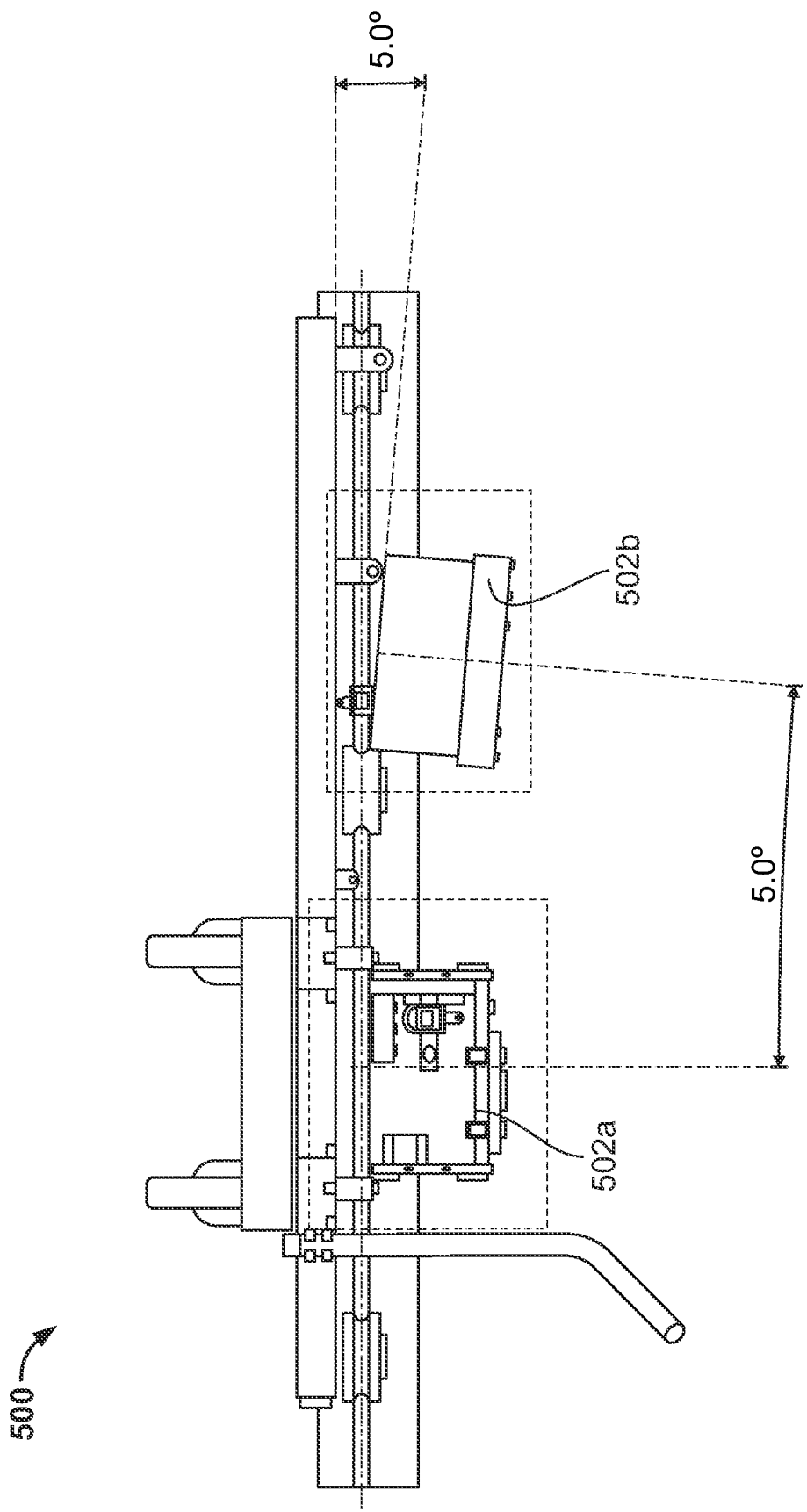

METHODS AND SYSTEMS FOR THE CONCURRENT GENERATION OF MULTIPLE SUBSTANTIALLY SIMILAR X-RAY BEAMS

CROSS-REFERENCE

The present application relies on U.S. Patent Provisional Application No. 63/261,991, titled "Methods and Systems for the Concurrent Generation of Multiple Substantially Similar X-Ray Beams" and filed on Oct. 1, 2021, for priority, which is herein incorporated by reference in its entirety.

FIELD

The present specification generally relates to radiographic imaging systems. More specifically the present specification relates to systems and methods for concurrently generating X-ray beams having substantially similar characteristics using an adjustable collimator.

BACKGROUND

Stereoscopic X-ray imaging methods are used to separate, in an image, each object in a detection space, which are located at different depths. The principle of stereoscopic X-ray imaging is based on the ability to perceive depth of a three-dimensional structure using binocular vision. The binocular vision is simulated by splitting the X-ray beam from a single source into two beams. The single X-ray beam is typically formed by two collimation slits that may be provided in a beam controller section of the radiographic imaging device. The two beams may be either symmetric or asymmetric with an angle between them.

U.S. Pat. No. 9,763,630, titled "Stereoscopic imaging systems and methods" provides "a stereoscopic imaging system, comprising: an X-ray source configured to emit a plurality of X-ray fan beams; a plurality of columns of detectors, wherein each column of detectors is arranged at a preset angle with respect to the X-ray source, and configured to detect a strength value of a respective one of the X-ray fan beams penetrating an object under inspection, and each column of detectors is configured to form a respective transmission image, when the object intersects, or moves along a direction intersecting with, the X-ray fan beams, with the preset angle being unchanged; and a reconstruction apparatus configured to select two transmission images from the formed transmission images, use the selected images to calculate depth information regarding the object and reconstruct a 3D image of the object based on the calculated depth information."

However, current stereoscopic imaging methods provide limited information about the material properties of an object that may be different from the material properties of another object in the same direction. The accurate identification of material properties is critical for security applications of the imaging systems.

Multi-energy imaging methods are used to distinguish different types of materials. Imaging systems using X-rays having multiple energies, are able to discriminate between materials of varying elemental composition. However, in cases where objects with differing compositions overlap each other, the properties of one object in the overlapping volume may dominate the attenuation absorption profile while the second object's attenuation characteristics may be difficult, if not impossible, to identify.

Methods for combining binocular stereoscopic imaging and multi-energy transmission methods to identify material properties of objects that overlap in the direction of an X-ray beam are well-known. U.S. Pat. No. 8,194,953, titled "Method and system of material identification using binocular stereoscopic and multi-energy transmission images" provides "material identification and imaging method using binocular stereoscopic and multi-energy transmission images comprise the following steps: 1) causing two angled X-ray beams to penetrate through objects under examination so as to obtain data of left and right transmission images, segmenting said left and right transmission images and matching the results of said segmentation; 2) creating a depth plane along the depth direction of the transmission images; 3) repeating the above process on transmission images of variation energy to obtain a depth plane of each depth plane for the variation energy; 4) merging the depth planes for different energy levels at the same position to obtain a depth plane for each depth plane and energy of a predetermined group of energy levels; 5) identifying the material of the objects for each of which a grey reconstruction in said depth plane succeeds."

However, current collimation systems that generate X-ray beams are unable to effectively generate multiple non-parallel X-ray beams from the same source having sufficiently similar beam characteristics further having minimized, yet similar, dose drop-offs at a given angle. As a result, these systems find limited application in security inspection systems, portals, baggage, and/or cargo inspection systems. Hence, there is need for collimation systems and methods that enable the generation of multiple non-parallel X-ray beams from the same source having sufficiently similar beam characteristics.

SUMMARY

The following embodiments and aspects thereof are described and illustrated in conjunction with systems, tools and methods, which are meant to be exemplary and illustrative, and not limiting in scope. The present application discloses numerous embodiments.

In some embodiments, the present specification describes an adjustable collimator device adapted to collimate a beam of energy emitted from a radiation source, comprising: an elongated body with a front-end and a rear-end; a first plurality of emission apertures equally spaced around a longitudinal axis extending through a center of the elongated body, wherein the longitudinal axis defines a zero-degree position, wherein the first plurality of emission apertures is placed proximate the rear-end of the elongated body, and wherein the first plurality of emission apertures is configured to receive a beam of energy entering the adjustable collimator device and sample the beam of energy generated; and a second plurality of apertures placed proximate the front-end of the elongated body, wherein the second plurality of apertures are adjustable such that a first of the second plurality of apertures can be configured to have a first angular offset relative to the zero-axis and a second of the second plurality of apertures can be configured to have a second angular offset relative to the zero-axis, and wherein the first angular offset is equal to or different from the second angular offset.

Optionally, the adjustable collimator device is configured to collimate the beam of energy such that a first energy beam and a second energy beam, separate from the first energy beam, are concurrently emitted from the adjustable collimator device, wherein the first energy beam and the second energy beam have substantially similar characteristics.

Optionally, the adjustable collimator device and the radiation source are rotated around a position of the radiation source by half of an angle of separation between the first energy beam and the second energy beam, to bring either one of the first energy beam or the second energy beam perpendicular to an object being imaged by the adjustable collimator device.

Optionally, the beam of energy is an X-ray beam.

Optionally, the second plurality of emission apertures comprises first and second movable apertures.

Optionally, the first movable aperture comprises two adjustable jaws that, in combination, define the first movable aperture and are configured to adjust the first movable aperture to a plurality of different angular offsets relative to the zero axis and wherein the second movable aperture comprises two adjustable jaws that, in combination, define the second movable aperture and are configured to adjust the second movable aperture to a plurality of different angular offsets relative to the zero axis such that the first movable aperture and second movable aperture concurrently generate X-ray beams equally offset from the zero axis.

Optionally, the first plurality of emission apertures comprises third and fourth fixed apertures.

Optionally, the two adjustable jaws of each of the first and second movable apertures are positioned such that the adjustable jaws do not occlude the beam of energy.

Optionally, the substantially similar characteristics of the first energy beam and the second energy beam include dose and energy.

Optionally, the first angular offset is in a range of 5 degrees to 10 degrees.

Optionally, the second angular offset is in a range of 5 degrees to 10 degrees.

In some embodiments, the present specification describes a radiographic imaging method comprising: positioning an adjustable collimator device near a radiation source configured to generate an X-ray beam, wherein the adjustable collimator device includes a first et of collimators and a second set of collimators; collimating the X-ray beam, using the first set of collimators, to concurrently generate a first X-ray beam and a second X-ray beam, wherein the first X-ray beam and the second X-ray beam are not parallel; collimating the first X-ray beam, using a first of the second set of collimators, to generate a third X-ray beam, wherein the third X-ray beam emanates from the collimator device at a first angle of separation with respect to a central axis of the collimator device; and collimating the second X-ray beam, using a second of the second set of collimators, to generate a fourth X-ray beam, wherein the fourth X-ray beam emanates from the collimator device at a second angle of separation with respect to the central axis.

Optionally, the first angle of separation is equal to the second angle of separation.

Optionally, the first set of collimators define first and second apertures of fixed width, and wherein the first and second apertures are positioned equidistant from the central axis.

Optionally, the second set of collimators define third and fourth apertures, and wherein widths of the third and fourth apertures are adjustable.

Optionally, the third aperture is defined by first and second adjustable jaws and the fourth aperture is defined by third and fourth adjustable jaws, wherein the first and second adjustable jaws are configured to adjust the third aperture to a plurality of different angular offsets relative to the central axis, and wherein the third and fourth adjustable jaws are configured to adjust the fourth aperture to a plurality of different angular offsets relative to the central axis.

Optionally, the first and second adjustable jaws as well as the third and fourth adjustable jaws are positioned within the collimator device such that the first, second, third and fourth adjustable jaws do not occlude the first and second X-ray beams.

Optionally, the third and fourth X-ray beams have substantially similar dose and energy characteristics.

Optionally, the first angle of separation is in a range of 5 degrees to 10 degrees.

Optionally, the second angle of separation is in a range of 5 degrees to 10 degrees.

Optionally, the method further comprises generating first scan data by detecting the third X-ray beam after the third X-ray beam passes through an object being scanned; generating second scan data by detecting the fourth X-ray beam after the fourth X-ray beam passes through the object; generating first and second image data by processing the first and second scan data, respectively; and using the first and second image data, determining material composition and depth corresponding to contents of the object.

The present specification also discloses systems and methods for detecting X-ray radiation and generating an image of an object by utilizing two angled X-ray beams generated by an adjustable collimator system. In some embodiments, the adjustable collimator system for collimating a beam of energy emitted from a radiation source comprises a first plurality of emission apertures equally spaced around a zero-degree axis along an elongated plate-like body, the first plurality of emission apertures includes a fixed aperture and a movable aperture, wherein the movable aperture is provided with adjustable jaws to adjust the aperture at different angles to obtain concurrent generation of multiple collimated X-ray beams from a single radiation source. The X-ray beam from the radiation source passes through the first plurality of apertures, the first plurality of apertures samples the X-ray beam emitted from the radiation source and the two angled collimated beams exit through the second plurality of apertures at the rear-end of the adjustable collimator system. The collimated beams thus generated are concurrent with an angle of separation between them. Optionally, in an embodiment, the first plurality of emission apertures is made of materials such as but not limited to lead, tungsten, gold or uranium thereof. Moreover, the angle of separation between the two concurrent collimated beams generated by the adjustable collimator system is less than 10 degrees. Preferably the angle of separation between the two concurrent collimated beams generated by the adjustable collimator system is in the range of 5 degrees to 10 degrees.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 5 illustrates a top down or plan view of a radiation detection module, according to an embodiment of the present specification;

DETAILED DESCRIPTION

Figure 1:
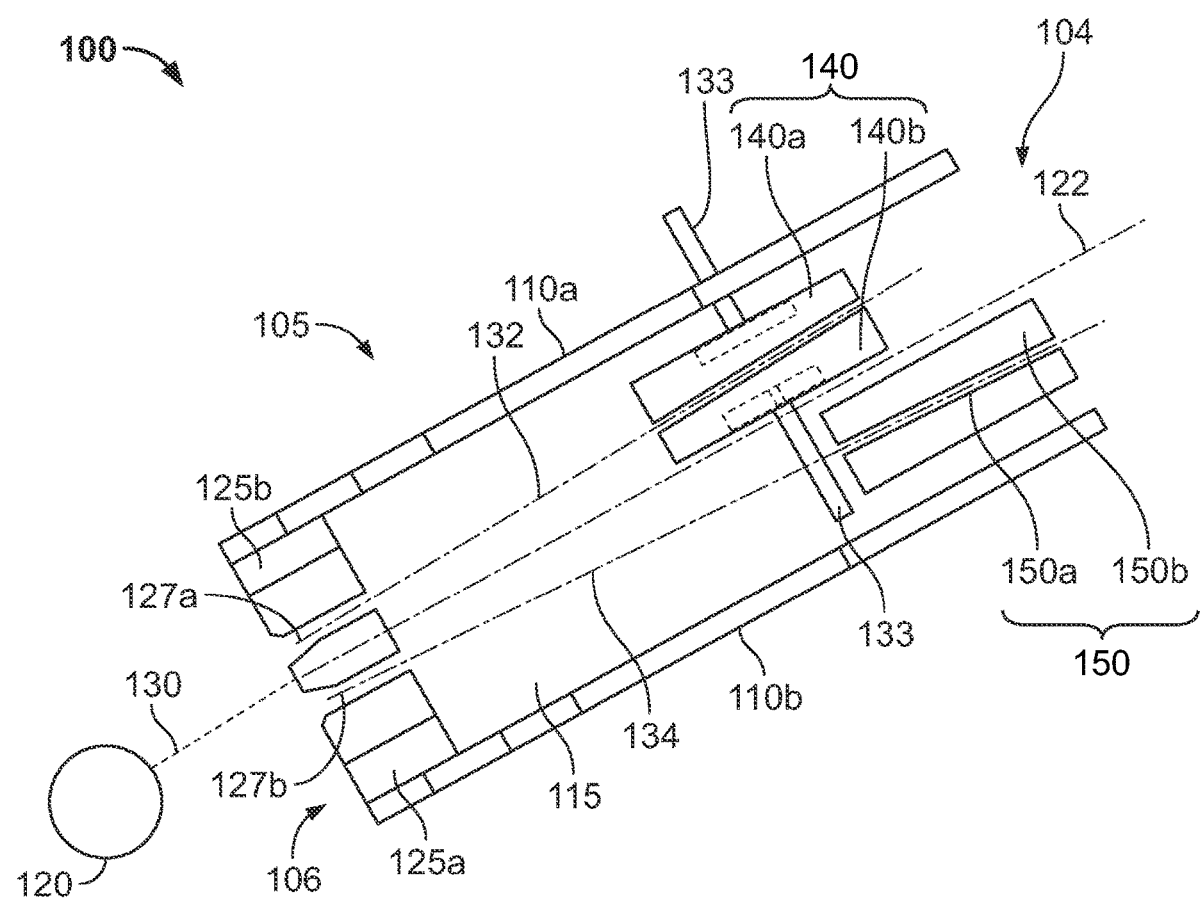
FIG. 1 illustrates an internal cross-sectional view of an adjustable collimator system, according to an embodiment of the present specification.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

In some embodiments, the present specification describes systems and methods for generating an image of an object by employing two angled X-ray beams generated by a radiographic imaging system. According to an aspect, the radiographic imaging system comprises positioning an adjustable collimator system near a radiation source with a LINAC target emitting radiation, collimating the radiation emitted from the LINAC target using the adjustable collimator system, thus generating two concurrent collimated beams simultaneously with a predefined, yet customizable, angle of separation between them, with each beam having beam characteristics substantially similar to each other. The emitted collimated beams of X-ray are poly-energetic and consists of a wide range of energies (ranging from 0 eV up to a maximum output of the LINAC), having a short wavelength and high frequencies. Furthermore, the radiographic imaging method consists of detecting the radiation that passes through the adjustable collimator system using a radiation detection module and processing an image recorded by the radiation detection module, using an image acquisition system and producing a desired image using a computer processing system thereby determining the material depth which aids in composition calculation of one or more objects in a detection space.

In some embodiments, the present specification is also directed toward systems and methods for detecting an image of an object by employing two angled X-ray beams generated by a radiographic imaging system. According to an aspect, the radiographic imaging method comprises the steps of generating two X-ray beams having an angle therebetween, using an adjustable collimation system, and directing the two angled X-ray beams to penetrate through the object under inspection in order to obtain transmission data. The transmission data is then analyzed to determine the material depth and composition of the object being inspected.

FIG. 1 is a plan cross-sectional view of an adjustable collimator system 100, in accordance with some embodiments of the present specification. In embodiments, the adjustable collimator system 100 is configured as a double-slit secondary collimator. The system 100 includes an elongated plate-like body 105 having first and second side-plates 110a, 110b positioned substantially parallel to each other and defining a gap, passage or channel 115 between the plates 110a, 110b. The body 105 is coupled to an X-ray source 120 such that a rear-end 106 is positioned proximate to the X-ray source 120 and a front-end 104 is positioned distal from the X-ray source 120. In some embodiments, the X-ray source 120 is a LINAC. A central axis 122 is indicative of a direction of a primary X-ray beam from the source 120 and is representative of a 0 degrees reference. It should be appreciated that, in some embodiments, an internal primary collimator of the LINAC source 120 is modified to remove a central axis aperture and, instead, introduce two separate apertures at equal angles from the center.

The collimator system 100 includes a first set of fixed collimating jaws 125a, 125b positioned proximate the rear-end 106 and that extend between the first and second side-plates 110a, 110b. The first set of collimating jaws 125a, 125b define first and second slits, apertures or openings 127a, 127b that serve to simultaneously or concurrently generate first and second non-parallel X-ray fan beams 132, 134. In some embodiments, the first and second slits, apertures or openings 127a, 127b are positioned equidistant from the central axis 122. In some embodiments, a width of the first and second slits, apertures or openings 127a, 127b is predefined and fixed. In some embodiments, the first and second slits, apertures or opening 127a, 127b are made of materials such as, but not limited to, lead, tungsten, gold or uranium.

It should be appreciated that the first set of collimating jaws 125a, 125b provide a "crude" collimation, mainly also catching scatter off the surface of the LINAC shielding.

The collimator system 100 further includes a second set of adjustable collimating jaws 140, 150. The collimating jaws 140 are coupled to the first side-plate 110a and include two displaceable diaphragm plates or jaws 140a, 140b defining a third slit. The collimating jaws 150 are coupled to the second side-plate 110b and include two displaceable diaphragm plates or jaws 150a, 150b defining a fourth slit. The diaphragm plates or jaws 140a, 140b and 150a, 150b of the respective collimators 140, 150 are movable relative to one another to modulate and achieve desired widths of the third and fourth slit openings. In some embodiments, the diaphragm plates or jaws 140a, 140b, 150a, 150b are offset along a direction of X-ray emission to allow for location of adjustment rods 133 (that connect the collimating jaws 140 and 150 to the sides 110a, 110b of the secondary collimator assembly 100) to not occlude the X-ray beam path.

It should be appreciated that the second set of collimating jaws 140, 150 collimate the respective X-ray beams 132, 134 down so that they only impinge on the front of the crystals on respective detector arrays.

During operation, the first X-ray fan beam 132 is collimated by the collimating jaws 140 while the second X-ray fan beam 134 is collimated by the collimating jaws 150 so that the first and second X-ray fan beams 132, 134 emanate from the system 100 at desired angles of separation with respect to the central axis 122 before entering a scan tunnel. In various embodiments, the third and fourth slits defined by the second set of collimating jaws 140, 150 are spatially separated from each other so that the first and second X-ray fan beams 132, 134 have the desired angles of separation with reference to the central axis 122.

In accordance with some aspects of the present specification, the first and second X-ray fan beams 132, 134 exiting the adjustable collimator system 100 possess substantially similar beam characteristics referred to as dose and energy, accounting for a symmetric "roll-off" in both dose and energy at equal angular displacements from the central axis 122 of X-ray generation. It should be appreciated that the spatial separation of the third and fourth slits has a bearing on changes in the X-ray spectrum of the first and second X-ray fan beams 132, 134 when measured at different angles of emission. Accordingly, in some embodiments, the spatial position (within the collimator system 100) and relative separation of the third and fourth slits is achieved so as to offset the first X-ray fan beam 132 by a first angle of separation 'A1' from the central axis 122 and the second X-ray fan beam 134 by a second angle of separation 'A2' from the central axis 122.

In some embodiments, the relative location of the two points of X-ray emission from the LINAC can be configured to minimize differences in energy and dose. In some embodiments, the first angle of separation is equal to the second angle of separation and each of the first and second angles of separation ranges from 1 degree to 5 degrees from the central axis 122. In some embodiments, a sum of the first and second angles of separation (that is, A1+A2) is in a range of 5 degrees to 10 degrees. In some embodiments, a sum of the first and second angles of separation (that is, A1+A2) is not greater than 10 degrees. In some embodiments, a sum of the first and second angles of separation (that is, A1+A2) is in a range of 1 degree to 20 degrees, or any numerical increment therein.

In embodiments where both first and second X-ray fan beams 132, 134 are offset from the central axis 122, the radiation source 120 and the collimator assembly 100 are rotated so that one of the first and second X-ray beams 132, 134 is imaging an object under inspection, such as, for example, cargo, at 90 degrees. This results in first and second scanned images, corresponding to the first and second X-ray beams 132, 134, that are substantially similar in performance (such as, but not limited to, intensity, contrast, sharpness) since dose and energy (of the first and second X-ray beams 132, 134) is substantially symmetrical around the 0 degree central axis 122.

In some embodiments, the primary X-ray beam is sampled by the first set of fixed collimating jaws 125a, 125b to emit both the first X-ray fan beam 132 substantially along the central axis 122 (and more specifically, at a 0-degree angle) and the second X-ray fan beam 134. The first X-ray fan beam 132 is further collimated by the collimating jaws 140 for shaping the width of the beam and the second X-ray fan beam 134 is further collimated by the collimating jaws 150 and eventually emitted at an offset or angle of separation from the central axis 122. Thus, in such embodiments, the first aperture 127a is along the central axis 122 while the second aperture 127b is at a distance from the central axis 122 (so that the first X-ray beam 132 is now emitted along the central axis 122 and is collimated by the jaws 140 for shaping the width of the beam 132). Consequently, the first X-ray fan beam 132 yields the highest dose and highest energy while the second X-ray fan beam 134 has a drop off in energy and dose resulting in a corresponding off-axis scan image having performance capabilities different from the scan image corresponding to the first X-ray fan beam 132.

Figure 2A:
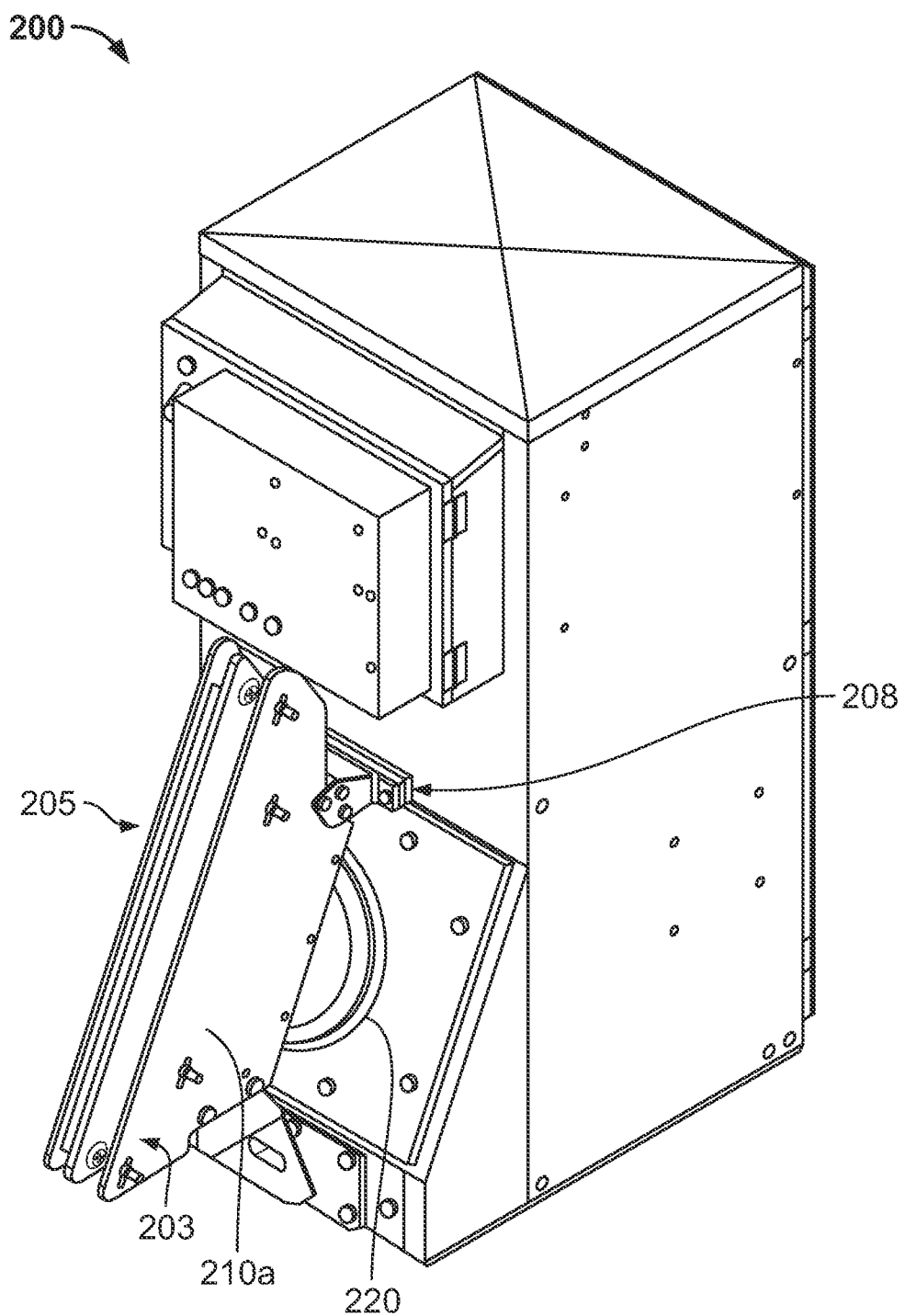
FIG. 2A illustrates a perspective view of an adjustable collimator attached to a radiation source, according to an embodiment of the present specification.
Figure 2B:
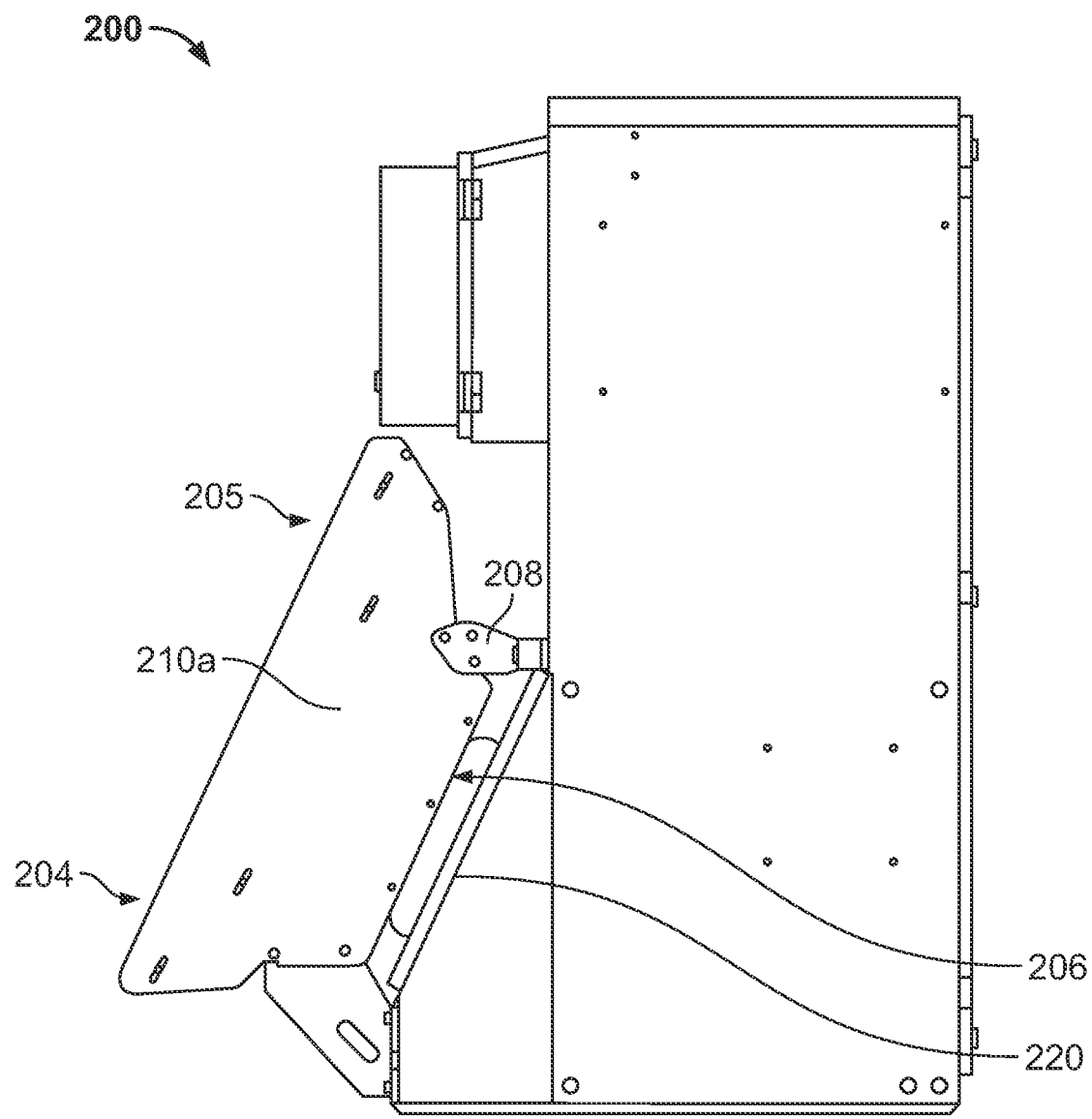
FIG. 2B illustrates a side view of an adjustable collimator attached to a radiation source, according to an embodiment of the present specification.
Figure 2C:
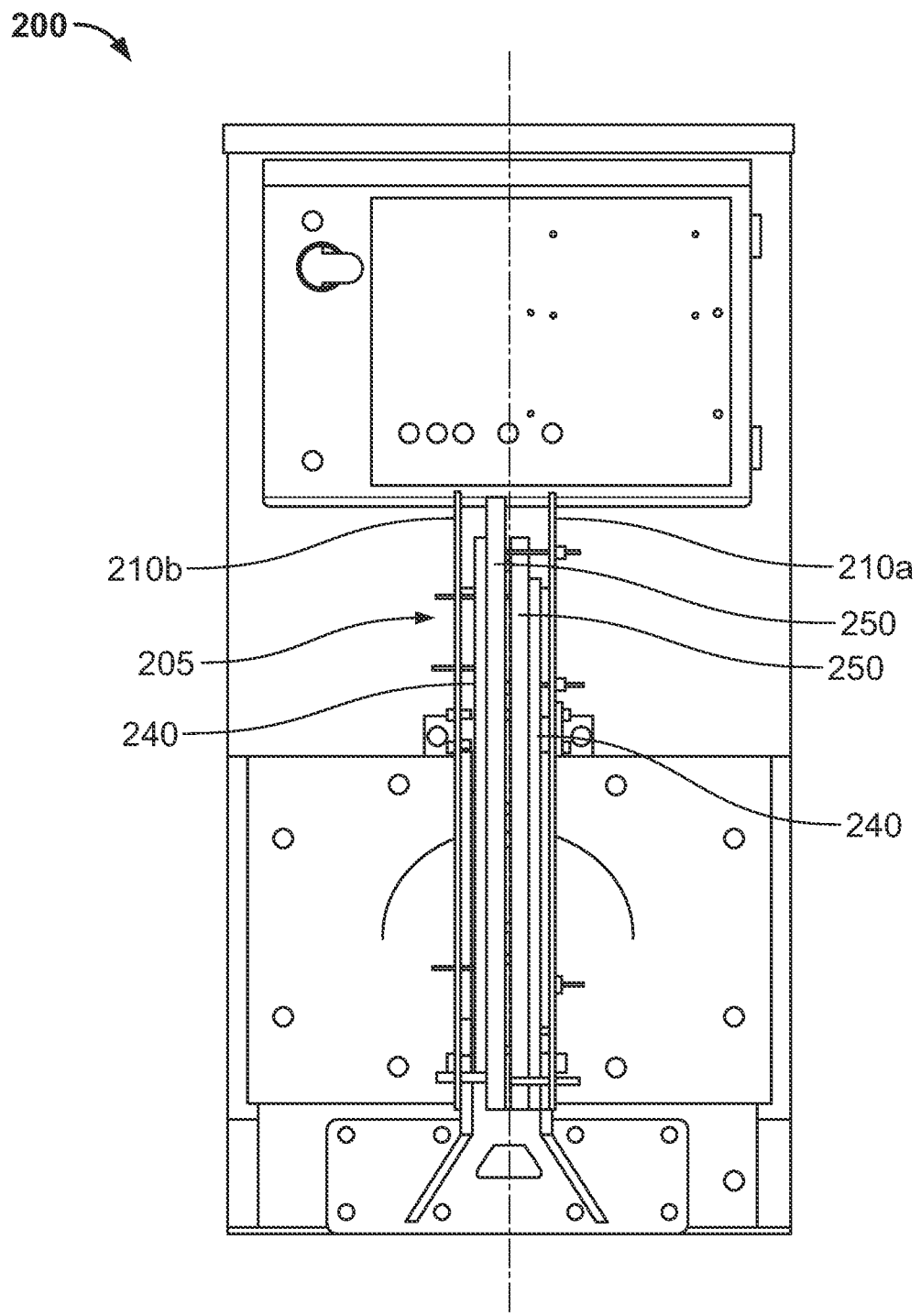
FIG. 2C illustrates a front view of an adjustable collimator attached to a radiation source, according to an embodiment of the present specification.

FIGS. 2A, 2B and 2C respectively illustrate perspective, side and front views of an adjustable collimator system 205 attached to a radiation source 220, in accordance with some embodiments of the present specification. Referring to FIGS. 2A, 2B and 2C simultaneously, the adjustable collimator system 205 includes an elongated plate-like body 203 having first and second side-plates 210a, 210b. The adjustable collimator system 205 is coupled or attached to the radiation source 220 using a top mount pack 208. In embodiments, the top mount pack is comprised of aluminum. In embodiments, the pack is structured as an L-shaped rack and includes a first portion for attachment to a first structure, such as the radiation source, and a second portion, perpendicular to the first portion, for attachment to a second structure, such as the adjustable collimator system. In embodiments, the top mount pack includes a mating hole and screw attachment system. In further embodiments, the top mount pack is used to provide at least one of the following: 1) a solution specific to a linac assembly to allow for attachment of a secondary collimator and/or 2) ensuring a minimum vibration/movement of the secondary collimator during operation.

As described earlier with reference to FIG. 1, the adjustable collimator system 205 includes a first set of fixed collimating jaws (not visible) positioned proximate the radiation source 220 (and towards a rear-end 206 of the system 205) along with a second set of adjustable collimating jaws 240, 250 positioned distal from the radiation source 220 (and towards a front-end 204 of the system 205). In accordance with some embodiments, width of the apertures or slits in the first set of collimating jaws is predefined and fixed whereas widths of the apertures or slits of the second set of collimating jaws 240, 250 are adjustable by moving two pairs of displaceable diaphragm plates or jaws of the second collimating jaws 240, 250.

During a scanning operation, a primary X-ray beam generated by the radiation source 220 is split by two slits or apertures of the first set of fixed collimating jaws into concurrent first and second X-ray fan beams. Further, the first X-ray fan beam is collimated by the adjustable collimating jaws 240 to exit the front-end 204 at a first angle of separation from a central longitudinal axis (identified as axis 122 in FIG. 1) of the collimator system 205 while the second X-ray fan beam is collimated by the adjustable collimating jaws 250 to exit the front-end 204 at a second angle of separation from the central longitudinal axis. The displaceable jaws of the second set of collimators 240, 250 are adjusted to modulate angles and/or widths of their respective slits or apertures in order to obtain desired first and second angles of separation.

Figure 3:
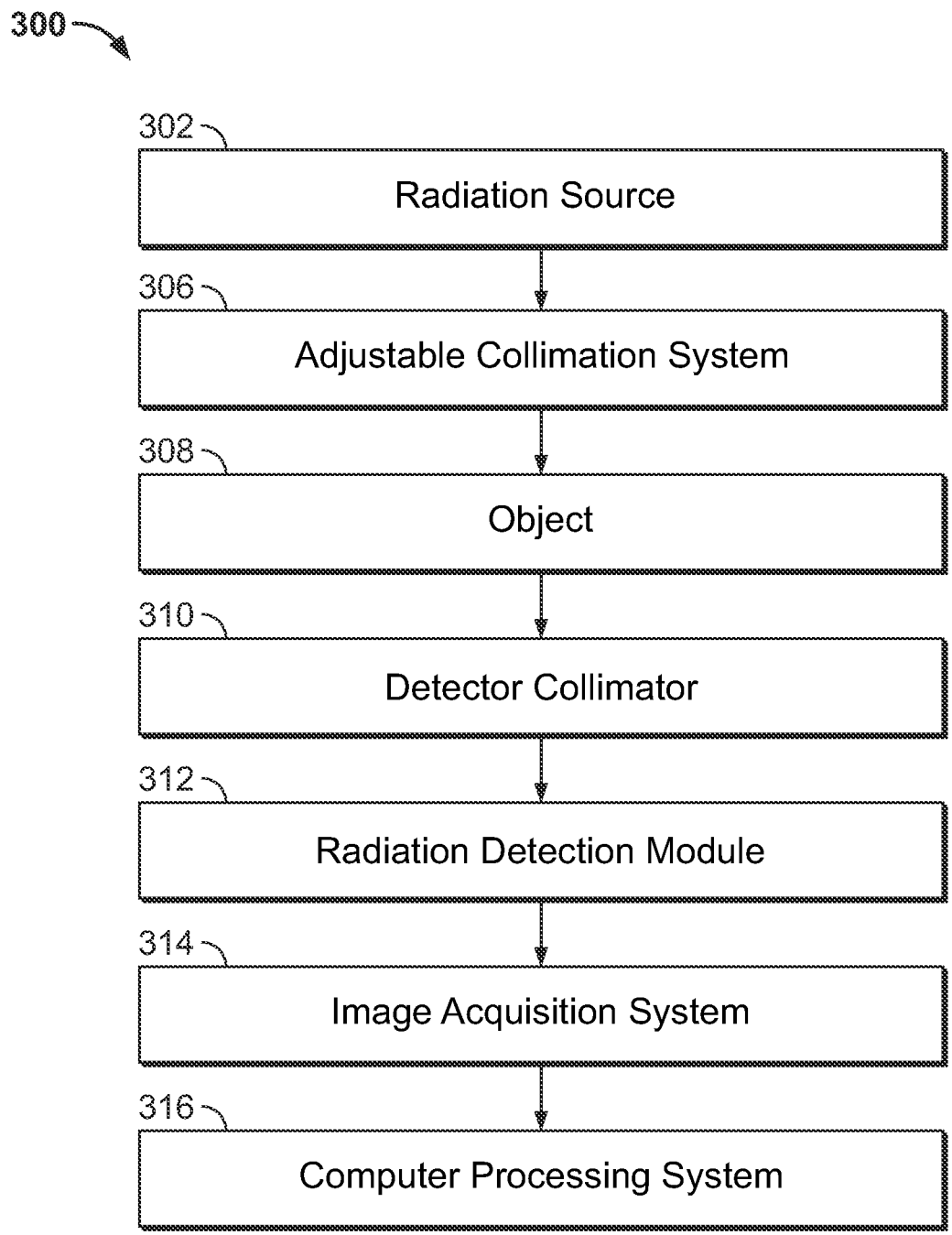
FIG. 3 illustrates an architectural representation of a radiographic imaging system, according to an embodiment of the present specification.

According to one embodiment of the present invention, FIG. 3 illustrates a block diagram representation of a radiographic imaging system 300 coupled with an adjustable collimator system 306. The radiographic imaging system 300 comprises of a radiation source 302, an adjustable collimator system 306, an object being inspected 308, detector collimators 310, a radiation detection module 312, an image acquisition system 314 and a computer processing system 316. The radiation source 302 is an X-ray generator that generates X-rays of different energy levels that are collimated by the adjustable collimator system 306 before being incident on the target 304. The adjustable collimator system 306 aids in sampling the X-ray generated from the radiation source 302 into two beam sectors with a predefined angle between them. In addition, the radiographic imaging system 300 consists of target detector collimators 310 in order to reduce the scattering of X-ray radiation. The radiation detection module 312 receives the X-rays of different energy levels and converts them into electrical signals. The image acquisition system 314 receives the electrical signals from the radiation detection module 312 and generates image data from the electrical signals. The computer processing system 316, which receives the image data from the image acquisition system 314, processes the image data at different energy levels in order to determine the depth and composition of material contained within the object 308.

Figure 4A:
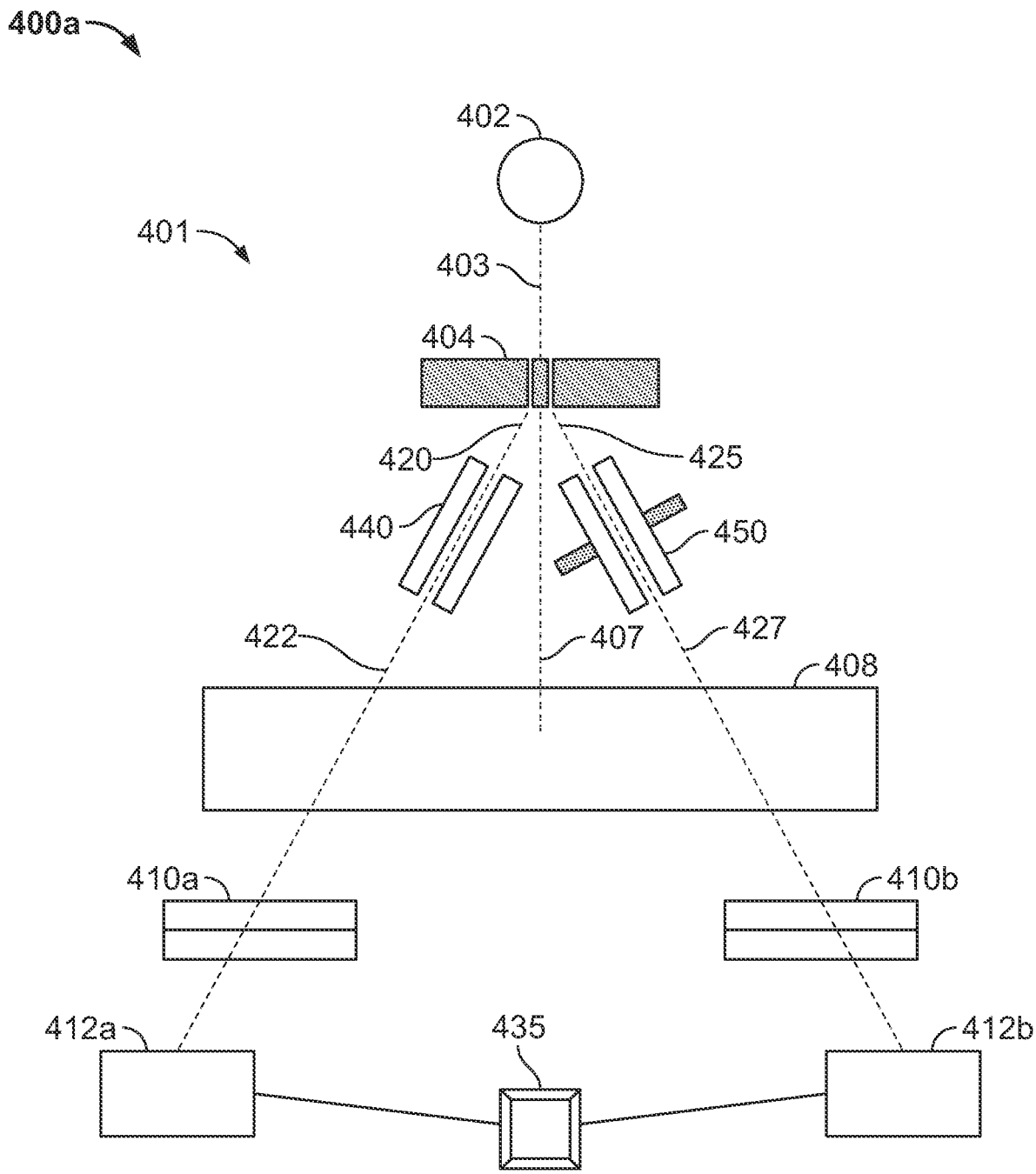
FIG. 4A illustrates a top view of a first configuration of the radiographic imaging system of FIG. 3, according to an embodiment of the present specification.

According to one embodiment of the present specification, FIG. 4A illustrates a top view of a first configuration 400a of a radiographic imaging system 401 coupled to an adjustable collimator system. The radiographic imaging system 401 with reference to FIG. 4A illustrates a first fixed collimator 404 splitting a primary X-ray beam 403 emanating from a radiation source 402 into first and second X-ray beams 420, 425. The first and second X-ray beams 420, 425 are further collimated by second set of adjustable slit collimators 440, 450 into two angled beams 422, 427. The two collimation slits of the second set of collimators 440, 450 shape the two X-ray beams 420, 425 to generate two angled beams 422, 427 having respective first and second angles of separation with a central axis 407. In some embodiments, each of the first and second angles of separation ranges from 1 degree to 5 degrees from the central axis 407. In some embodiments, a total angle of separation between the two beams 422, 427 ranges from 5 degrees to 10 degrees. In some embodiments, a total angle of separation between the two beams 422, 427 is less than or equal to 10 degrees.

Target detector collimators 410a, 410b help reduce the scattering of X-ray beams 422, 427 and cross-talk. A radiation detection module includes a first detector array 412a to receive the X-ray beam 422 after transmission through an object 408 and a second detector array 412b to receive the X-ray beam 427 after transmission through the object 408. The first and second detector arrays 412a, 412b generate corresponding first and second scan signals that are transmitted to corresponding image acquisition systems that generate corresponding first and second image data. Thereafter, a computer processing system 435 carries out processing of the first and second image data in order to determine the material depth which aids in composition calculation of various materials or content of the object (or detection space).

Figure 4B:
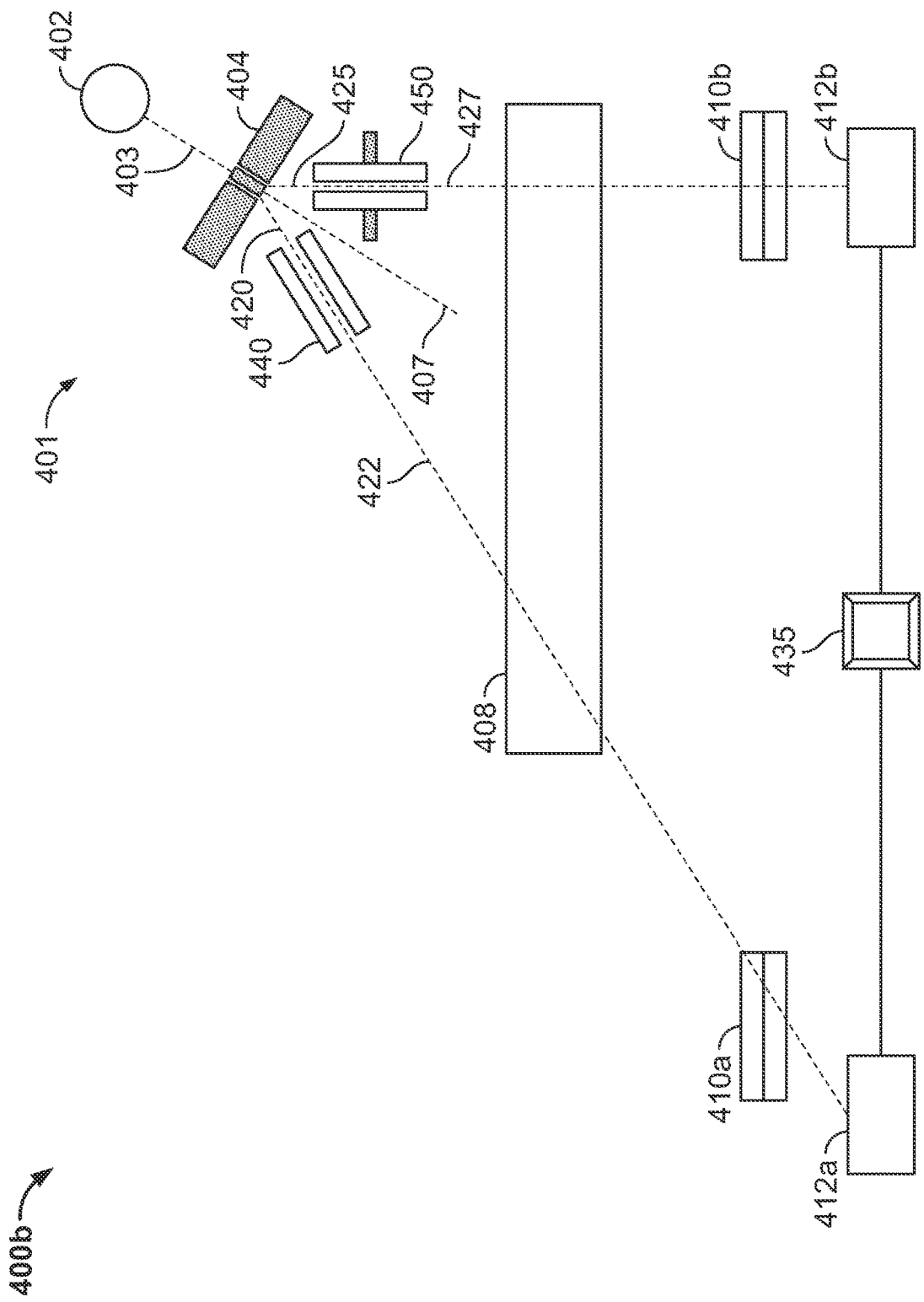
FIG. 4B illustrates a top view of a second configuration of the radiographic imaging system of FIG. 3, according to an embodiment of the present specification.

According to another embodiment of the present specification, FIG. 4B illustrates a top view of a second configuration 400b of the radiographic imaging system 401 coupled to the adjustable collimator system. To avoid repetition, like numerical references in FIGS. 4A and 4B refer to like elements. In the second configuration 400b, the first and second X-ray beams 420, 425 are offset relative to the 0-degree central axis 407 (such that the first and second beams have an angle of separation between them as in the first configuration 400a). This is done in order to achieve substantially similar beams. However, without any source rotation, this would result in the generation of two images, neither of which give a view "perpendicular" to the direction of travel of the vehicle under inspection. Therefore, in embodiments, at the same time as the offset of first and second X-ray beams 420, 425 is achieved relative to 0° central axis 407, the entire source 402 and adjustable collimation system 440, 450 are rotated around the source position (that is, yaw) by half (½) the angle of separation (existing in the first configuration 400a) between the first and second beams 420, 425. In other words, the source 402 and adjustable collimation system 440, 450 are rotated so that one of the first and second X-ray beams, that is the X-ray beam 427 in FIG. 4B, is imaging the object 408 at 90 degrees while still maintaining the energy equivalence between the first and second X-ray beams 422, 427. Rotating the source assembly including 402 and 440, 450, by an amount equal to the offset of each beam from the central axis, brings one beam (in this case beam 427) back to perpendicular and the other (beam 422) at an angle of the total separation of the two beams. This embodiment enables at least one image that is of a standard geometry of 90 degrees to the object being imaged. Thus, the second configuration 400b is also characterized by the first and second X-ray beams 422, 427 being substantially similar in performance (such as, but not limited to, intensity, contrast, sharpness) since dose and energy (of the first and second X-ray beams 422, 427) is substantially symmetrical around the 0-degree central axis 407.

According to one embodiment of the present invention, FIG. 5 illustrates a top down or plan view of a radiation detection module 500. The radiation detection module 500 includes left detector array 502a and right detector array 502b arranged at a pre-calibrated angle. Preferably the pre-calibrated angle between both the arrays 502a and 502b ranges from 1 degree to 10 degrees and preferably from 5 degrees to 10 degrees. The left detector array 502a and right detector array 502b are arranged such that both the arrays maintain same source to array distance. In order to maintain the same source to array distance the radiation detection module 500 needs to be moved closer to the scan tunnel of a radiographic imaging system and maintain a pre-calibrated angle of 1 degree to 10 degrees or 5 degrees to 10 degrees between both the arrays of the radiation detection module 500.

Moreover, the radiation detection module 500 directly faces the two angled X-ray beams emitted from the adjustable collimator system. Hence, the detection module 500 scans and examines the object under inspection in a symmetric fashion and transmits the scan signals to a corresponding image acquisition system.

Figure 6:
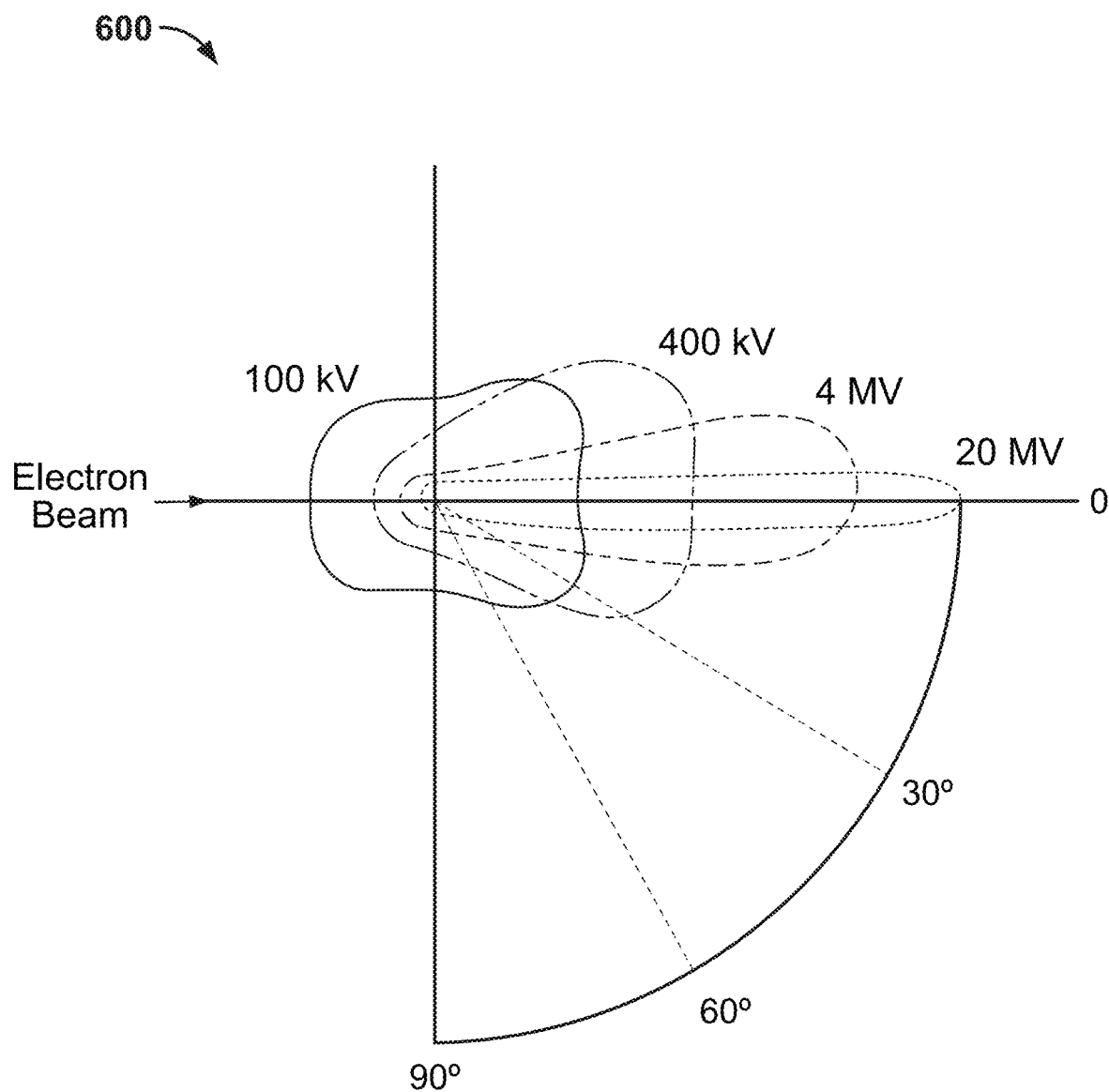
FIG. 6 illustrates a spatial distribution of X-ray photons caused around an off-axis target.

According to one embodiment of the present invention, FIG. 6 illustrates a spatial distribution 600 of X-ray photons generated around a target. FIG. 6 demonstrates that as the X-ray energy increases, the amount of forward emission increases and as one moves away from the 0-degree angle there is a drop in energy and dose. The two collimation slits (corresponding to the displaceable second set of collimators 140, 150 of FIG. 1) of the adjustable collimation system shape the X-ray beam emitted from the radiation source into two ray beams with an angle between them. The angle of separation between the two X-ray beams generated by the adjustable collimation system is preferably in the range of 1 degree to 10 degrees, although it may be of any angular separation.

Changes in the X-ray spectrum measured at different angles of emission are referred to as dose and energy roll off. The embodiments of the present invention consider three different scenarios of splitting an X-ray beam emitted by the radiation source. With reference to FIG. 6, a first option is to maintain a first normal X-ray beam to be emitted in the direction of the electron beam which is 0 degrees, that yields the highest dose and highest energy. For example, the X-rays emitted in the direction of 0 degrees can be in a range of 20 MV. However, a second offset beam, which is not directed along the 0-degree direction but rather is offset from that direction by a predefined angle of separation (with reference to the 0 degree direction), experiences a drop off in energy and dose and therefore the first option results in two beams having substantially different characteristics.

A second option with reference to FIG. 6 is to offset both the first and second beams relative to a 0 degree centerline by, for example, positioning the adjustable collimation system, such that each of the beams is imaging the object at the same degree of offset. Therefore, the quality of X-ray inspection resulting from the two beams are closer in performance because the dose and energy are symmetrical around the 0-degree axis. In one embodiment, the preferred angle of separation between the two beams is not more than 10 degrees and is preferably equal to, or between, 1 degree to 10 degrees and more preferably in a range of 5 to 10 degrees. The benefit of a 1 degree to 10-degree separation is that, at 10 degrees or less, the dose drop off is limited and still provides sufficient penetrative capability. Additionally, from scanned image perspective, there is a desired optimal range of angles of separation for which a useful image would be generated. If the angle of separation is too small the realized benefits are negligible in identifying structures that are positioned on the 0 degree axis. Again, if the angle of separation is too large this would result in firing X-ray beams through too large an inspection volume, of an object under inspection, to reveal any additional information.

A third option with reference to FIG. 6 is to offset both the first beam and second beam relative to the 0-degree centerline (such that the first beam and the second beam have an angle of separation between them as described with reference to the second option above) and at the same time rotating the entire source and adjustable collimation system around the source position (that is, yaw) by half (½) the angle of separation between the first and second beams. In other words, the source and adjustable collimation system are rotated so that at least one of the first X-ray beam and second X-ray beam is imaging an object under inspection, such as, for example, cargo, at 90 degrees while still maintaining the energy equivalence between the first and second X-ray beams.

Figure 7:
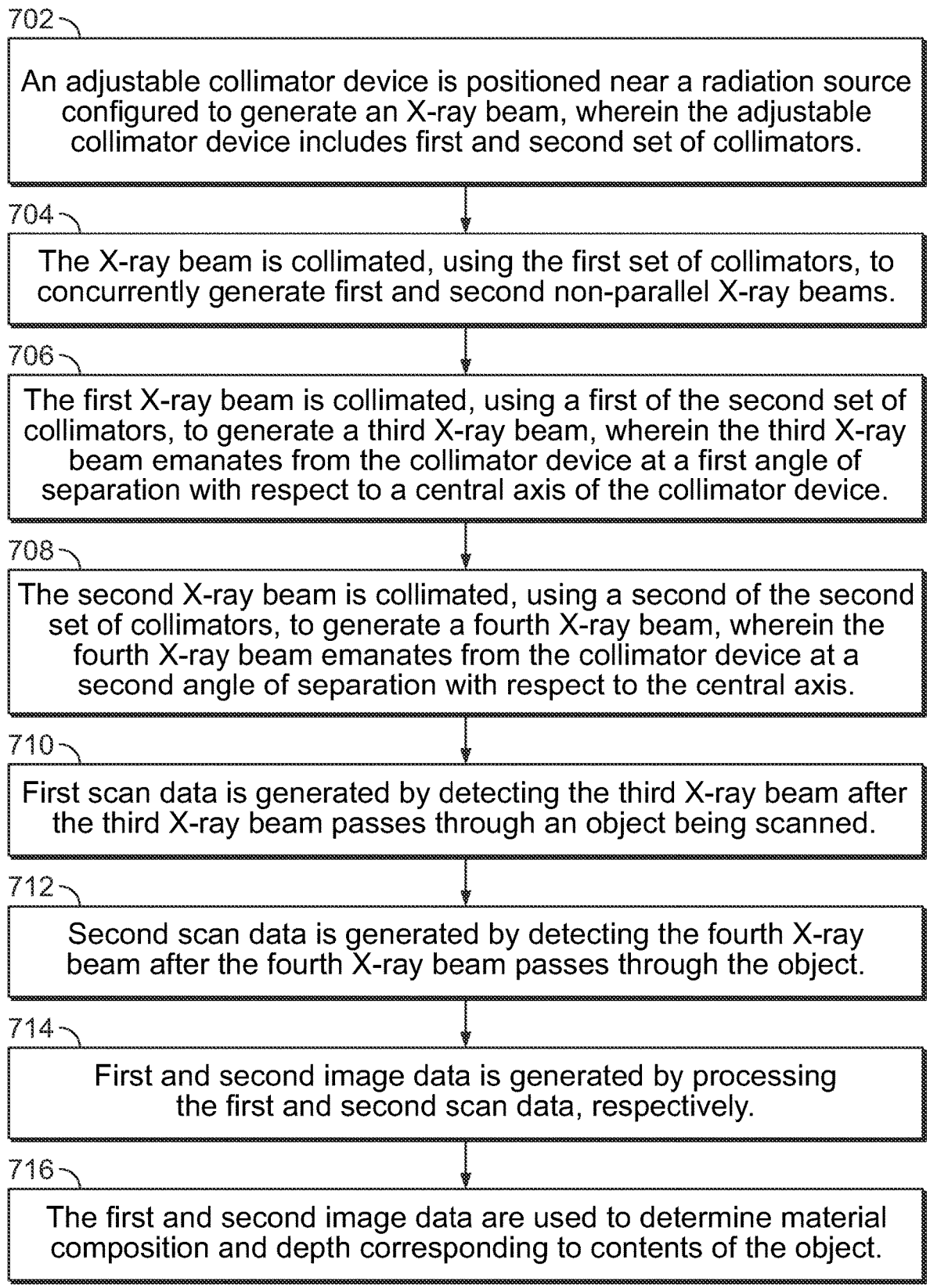
FIG. 7 is a flowchart of a plurality of exemplary steps of a method of using an adjustable collimator device to determine material composition and depth corresponding to contents of an object (or detection space), in accordance with some embodiments of the present specification.

FIG. 7 is a flowchart of a plurality of exemplary steps of a method of using an adjustable collimator device to determine material composition and depth corresponding to contents of an object (or detection space), in accordance with some embodiments of the present specification. At step 702, an adjustable collimator device is positioned near a radiation source configured to generate an X-ray beam, wherein the adjustable collimator device includes first and second set of collimators.

In some embodiments, the first set of collimators define first and second apertures of fixed width, and wherein the first and second apertures are positioned equidistant from a central axis of the collimator device. In some embodiments, the second set of collimators define third and fourth apertures, and wherein widths of the third and fourth apertures are adjustable. In some embodiments, the third aperture is defined by first and second adjustable jaws and the fourth aperture is defined by third and fourth adjustable jaws, wherein the first and second adjustable jaws are configured to adjust the third aperture to a plurality of different angular offsets relative to the central axis, and wherein the third and fourth adjustable jaws are configured to adjust the fourth aperture to a plurality of different angular offsets relative to the central axis.

In some embodiments, the first and second adjustable jaws as well as the third and fourth adjustable jaws are positioned within the collimator device such that the first, second, third and fourth adjustable jaws do not occlude the first and second X-ray beams.

At step 704, the X-ray beam is collimated, using the first set of collimators, to concurrently generate first and second non-parallel X-ray beams.

At step 706, the first X-ray beam is collimated, using a first of the second set of collimators, to generate a third X-ray beam, wherein the third X-ray beam emanates from the collimator device at a first angle of separation with respect to the central axis of the collimator device. At step 708, the second X-ray beam is collimated, using a second of the second set of collimators, to generate a fourth X-ray beam, wherein the fourth X-ray beam emanates from the collimator device at a second angle of separation with respect to the central axis.

In some embodiments, the first angle of separation is equal to the second angle of separation. In some embodiments, the first angle of separation is in a range of 5 degrees to 10 degrees. In some embodiments, the second angle of separation is in a range of 5 degrees to 10 degrees.

In some embodiments, the third and fourth X-ray beams have substantially similar dose and energy characteristics.

At step 710, first scan data is generated by detecting the third X-ray beam after the third X-ray beam passes through an object being scanned. At step 712, second scan data is generated by detecting the fourth X-ray beam after the fourth X-ray beam passes through the object. At step 714, first and second image data is generated by processing the first and second scan data, respectively. Finally, at step 716, the first and second image data are used to determine material composition and depth corresponding to contents of the object.

Figure 8:
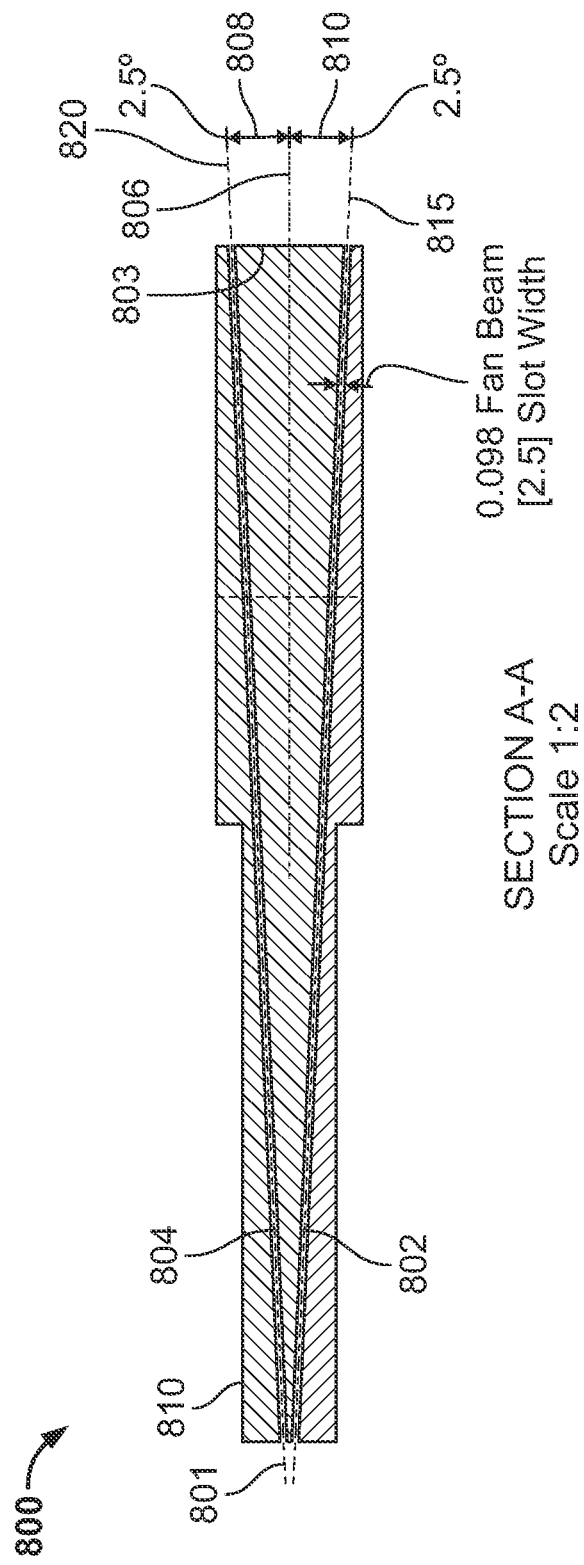
FIG. 8 illustrates a collimator insert having a predefined slot structure, in accordance with some embodiments of the present specification.

FIG. 8 shows a removable collimator insert 800, configured to be inserted into the shielding of an X-ray radiation housing, such as a primary shielding structure, inserted in a primary collimator of a LINAC or inserted within an existing slot extending outward from an electron beam target. The collimator insert 800 comprises a block of material 810 having two hollowed pathways or slits 802, 804 that are cored, carved, drilled or otherwise constructed within the block of material 810. The slits 802, 804 diverge at a predefined angle from each other. More specifically, the slits 802, 804 diverge distally from the entry point 801 in the collimator insert 800 at an angle of divergence relative to a central axis 806 where the angle of divergence is equal for both slits 802, 804. Therefore, upon exit 803 from the collimator insert 800 the resulting first and second fan beams 815, 820 have an equal displacement 808 and 810 relative to the central axis 806.

In accordance with some embodiments, the collimator insert 800 is a complementary modification (albeit the collimator insert will differ with different LINAC shielding configurations from different LINAC vendors) that allows for the generation of the first and second beams 815, 820 directly after the LINAC target where the X-ray beams are generated.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modifications.

The above examples are merely illustrative of the many applications of the systems and methods of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An adjustable collimator device adapted to collimate a beam of X-rays emitted from a radiation source, comprising:
   an elongated body with a front-end and a rear-end;
   a first plurality of emission apertures equally spaced around a longitudinal axis extending through a center of the elongated body, wherein the longitudinal axis defines a zero-degree position, wherein the first plurality of emission apertures is placed proximate the rear-end of the elongated body, and wherein the first plurality of emission apertures is configured to receive the beam of X-rays entering the adjustable collimator device; and
   a second plurality of emission apertures placed proximate the front-end of the elongated body, wherein the second plurality of apertures are adjustable such that a first of the second plurality of apertures can be configured to have a first angular offset relative to the zero-axis and a second of the second plurality of apertures can be configured to have a second angular offset relative to the zero-axis, and wherein each of the second plurality of apertures is formed by two jaws having lengths which extend in the same direction as the beam of X-rays such that the beam of X-rays is collimated to yield a first beam of X-rays and a second beam of X-rays, separate from the first beam of X-rays but with substantially similar characteristics, that are concurrently emitted from the adjustable collimator device.

2. The adjustable collimator device of claim 1, wherein the adjustable collimator device is configured to be rotated around a position of the radiation source by half of an angle of separation between the first beam of X-rays and the second beam of X-rays, to bring either one of the first beam of X-rays or the second beam of X-rays perpendicular to an object being imaged by the adjustable collimator device.

3. The adjustable collimator device according to claim 1, wherein the first of the second plurality of apertures and the second of the second plurality of apertures are configured to be movable.

4. The adjustable collimator device according to claim 3, wherein the two jaws of the first movable aperture are adjustable jaws that, in combination, define the first movable aperture and are configured to adjust the first movable aperture to a plurality of different angular offsets relative to the zero axis and wherein the two jaws of the second movable aperture are adjustable jaws that, in combination, define the second movable aperture and are configured to adjust the second movable aperture to a plurality of different angular offsets relative to the zero axis such that the first movable aperture and second movable aperture concurrently generate said first and second X-ray beams equally offset from the zero axis.

5. The adjustable collimator device according to claim 4, wherein the two adjustable jaws of each of the first moveable aperture of the second plurality of apertures and second movable apertures of the second plurality of apertures are positioned such that the adjustable jaws do not occlude the beam of X-rays.

6. The adjustable collimator device according to claim 1, wherein the first plurality of emission apertures comprises first and second fixed apertures.

7. The adjustable collimator device according to claim 1, wherein said substantially similar characteristics of the first beam of X-rays and the second beam of X-rays comprise dose and energy.

8. The adjustable collimator device according to claim 1, wherein the first angular offset is in a range of 5 degrees to 10 degrees.

9. The adjustable collimator device according to claim 1, wherein the second angular offset is in a range of 5 degrees to 10 degrees.

10. A radiographic imaging method comprising:
    positioning an adjustable collimator device near a radiation source configured to generate an X-ray beam, wherein the adjustable collimator device includes a first set of collimators and a second set of collimators, wherein the second set of collimators define a first aperture and a second aperture, wherein the first aperture is defined by first and second adjustable jaws and the second aperture is defined by third and fourth adjustable jaws and wherein each of the first, second, third, and fourth adjustable jaws have lengths which extend in the same direction as the beam of X-rays;

collimating the X-ray beam, using the first set of collimators, to concurrently generate a first X-ray beam and a second X-ray beam, wherein the first X-ray beam and the second X-ray beam are not parallel;

collimating the first X-ray beam, using a first of the second set of collimators, to generate a third X-ray beam, wherein the third X-ray beam emanates from the collimator device at a first angle of separation with respect to a central axis of the collimator device; and collimating the second X-ray beam, using a second of the second set of collimators, to generate a fourth X-ray beam, wherein the fourth X-ray beam emanates from the collimator device at a second angle of separation with respect to the central axis.

11. The method of claim 10, wherein the first angle of separation is equal to the second angle of separation.

12. The method of claim 10, wherein the first set of collimators define first and second apertures of fixed width, and wherein the first and second apertures are positioned equidistant from the central axis.

13. The method of claim 10, wherein widths of the first and second apertures of the second set of collimators are adjustable.

14. The method of claim 13, wherein the first and second adjustable jaws are configured to adjust the first aperture to a plurality of different angular offsets relative to the central axis, and wherein the third and fourth adjustable jaws are configured to adjust the second aperture to a plurality of different angular offsets relative to the central axis.

15. The method of claim 14, wherein the first and second adjustable jaws as well as the third and fourth adjustable jaws are positioned within the collimator device such that the first, second, third and fourth adjustable jaws do not occlude the first and second X-ray beams.

16. The method of claim 10, wherein the third and fourth X-ray beams have substantially similar dose and energy characteristics.

17. The method of claim 10, wherein the first angle of separation is in a range of 5 degrees to 10 degrees.

18. The method of claim 10, wherein the second angle of separation is in a range of 5 degrees to 10 degrees.

19. The method of claim 10, further comprising:

generating first scan data by detecting the third X-ray beam after the third X-ray beam passes through an object being scanned;

generating second scan data by detecting the fourth X-ray beam after the fourth X-ray beam passes through the object;

generating first and second image data by processing the first and second scan data, respectively; and using the first and second image data, determining material composition and depth corresponding to contents of the object.

* * * * *